United States Patent
Hong et al.

(10) Patent No.: US 10,472,418 B2
(45) Date of Patent: Nov. 12, 2019

(54) COMPOSITION FOR PREVENTING OR TREATING LUNG CANCER COMPRISING ANTIBODY AGAINST CD66C AND CHEMOTHERAPEUTIC AGENT

(71) Applicant: DINONA, Seoul (KR)

(72) Inventors: Kwon Pyo Hong, Cheongju (KR); Mi Hyang Shin, Seongnam (KR); Sangsoon Yoon, Seoul (KR); Gil Yong Ji, Seoul (KR); Yoo Ri Moon, Cheongju (KR)

(73) Assignee: Dinona, Seoul (KR)

( * ) Notice: Subject to any disclaimer, the term of this patent is extended or adjusted under 35 U.S.C. 154(b) by 0 days.

(21) Appl. No.: 15/161,395

(22) Filed: May 23, 2016

(65) Prior Publication Data

US 2017/0267757 A1    Sep. 21, 2017

(30) Foreign Application Priority Data

Mar. 15, 2016   (KR) ........................ 10-2016-0031167

(51) Int. Cl.
| | |
|---|---|
| *C07K 16/28* | (2006.01) |
| *A61K 45/06* | (2006.01) |
| *A61K 39/395* | (2006.01) |
| *C07K 16/30* | (2006.01) |
| *A61K 31/337* | (2006.01) |
| *A61K 9/50* | (2006.01) |
| *A61K 39/00* | (2006.01) |

(52) U.S. Cl.
CPC ........ *C07K 16/2803* (2013.01); *A61K 9/5068* (2013.01); *A61K 31/337* (2013.01); *A61K 39/3955* (2013.01); *A61K 39/39558* (2013.01); *A61K 45/06* (2013.01); *C07K 16/3023* (2013.01); *A61K 2039/505* (2013.01); *C07K 2317/34* (2013.01); *C07K 2317/70* (2013.01); *C07K 2317/73* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| | | | |
|---|---|---|---|
| 2003/0235582 A1* | 12/2003 | Singh | A61K 39/39541 424/141.1 |
| 2011/0212095 A1 | 9/2011 | Song et al. | |
| 2013/0224210 A1* | 8/2013 | Adamkewicz | A61K 39/3955 424/139.1 |

FOREIGN PATENT DOCUMENTS

| | | |
|---|---|---|
| KR | 10-2005-0065587 | 6/2005 |
| KR | 10-2011-0098593 | 9/2011 |

OTHER PUBLICATIONS

Volk et al. (Neoplasia, 13(4):327-338, 2011).*
Kwon Pyo Hong, et al., "Therapeutic effect of anti CEACAM6 monoclonal antibody against lung adenocarcinoma by enhancing anoikis sensitivity.", Biomaterials 67, Oct. 2015, pp. 32-41.
Mulshine, J.L. and Sullivan, D.C. "Clinical practice. Lung cancer screening." N. Engl. J. Med., Jun. 30, 2005, 352(26): pp. 2714-2720.
Alan Sandler et al, "Paclitaxel-Carboplatin Alone or with Bevacizumab for Non-Small-Cell Lung Cancer", The New England Journal of Medicine, 2006, 355, p. 2542-50.

* cited by examiner

*Primary Examiner* — Nelson B Moseley, II
(74) *Attorney, Agent, or Firm* — Lex IP Meister, PLLC

(57) ABSTRACT

A use of prevention or treatment of lung cancer including an antibody specifically recognizing CD66c in lung cancer or its antigen-binding fragment and a chemotherapeutic agent is provided.

6 Claims, 27 Drawing Sheets

Specification includes a Sequence Listing.

Fig. 1

CD66c Genebank Protein No. AAH05008

```
  1 MGPPSAPPCR LHVPWKEVLL TASLLTFWNP PTTAKLTIES TPNNVAEGKE VLLLAHNLPQ
 61 NRIGYSWYKG ERVDGNSLIV GYVIGTQQAT PGPAYSGRET IYPNASLLIQ NVTQNDTGFY
121 TLQVIKSDLV NEEATGQFHV YPELPKPSIS SNNSNPVEDK DAVAFTCEPE VQNTTYLWWV
181 NGQSLPVSPR LQLSNGNRTL TLLSVKRNDA GSYECEIQNP ASANRSDPVT LNVLYGPDVP
241 TISPSKANYR PGENLNLSCH AASNPPAQYS WFINGTFQQS TQELFIPNIT VNNSGSYMCQ
301 AHNSATGLNR TTVTMITVSG SAPVLSAVAT VGITIGVLAR VALI
```

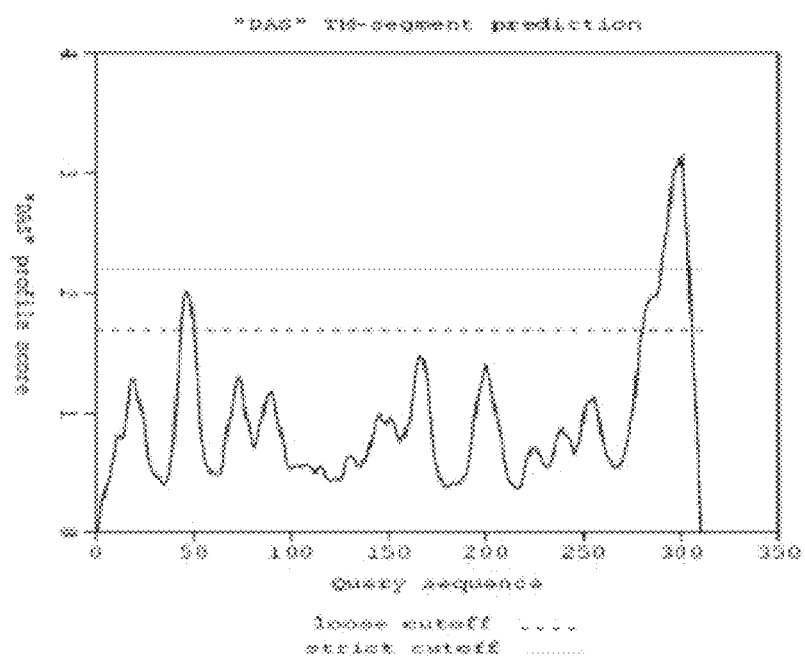

Fig. 4
A. anti-CD66c mAb (AP11) coating – method #1
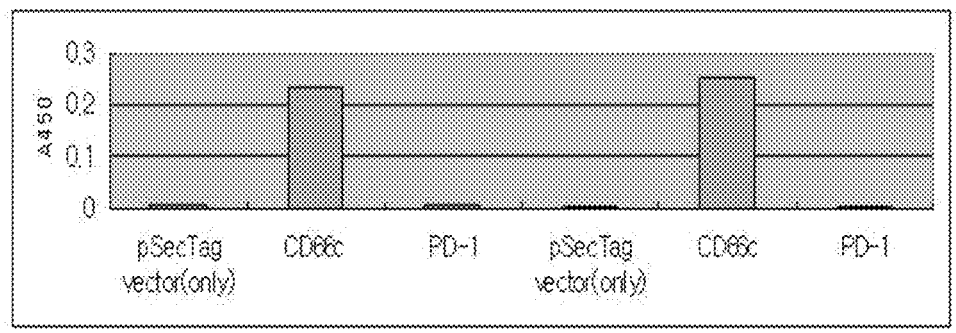
B. anti-Human Ig Fc coating – method #2
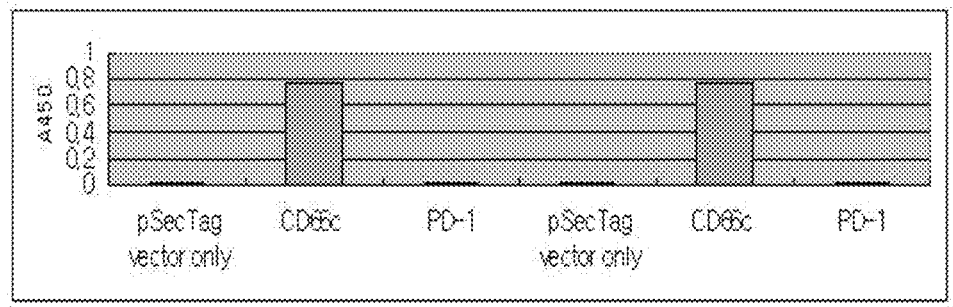
C. anti-Human Ig coating – method #3
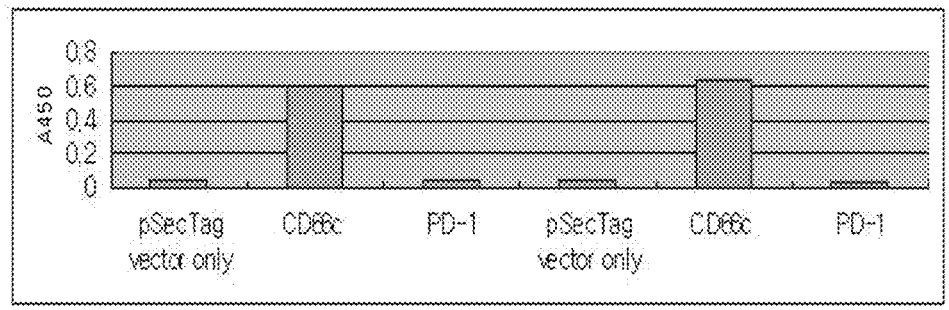

Fig. 14

Fig. 17
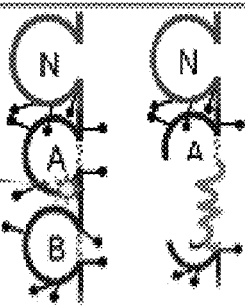
(1) Full length
(2) BI : A rear 30% ~ B fore 80% deleted
(3) HPK : N all ~ A fore 50% deleted Fig. 21
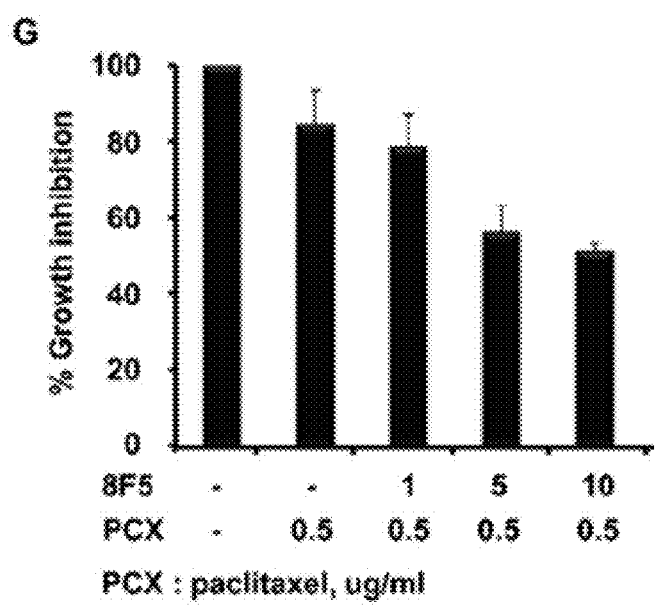
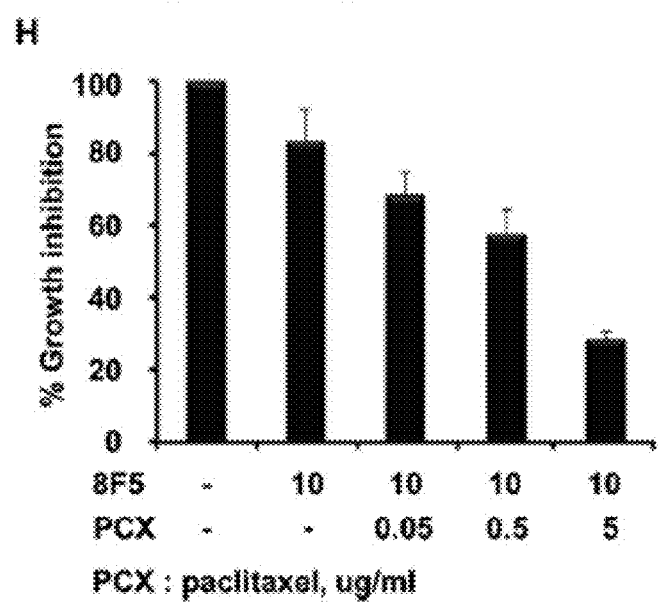

Fig. 25b
Photographs at day 26 and 33
PBS (26 days)
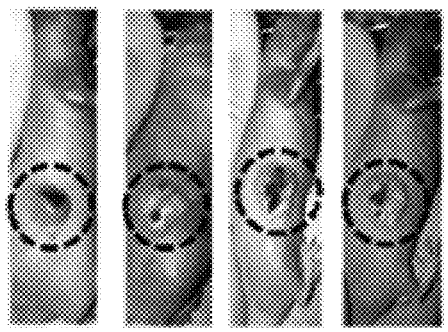
1  #2  #3  #4  #5
8F5 + PCX (33 days)
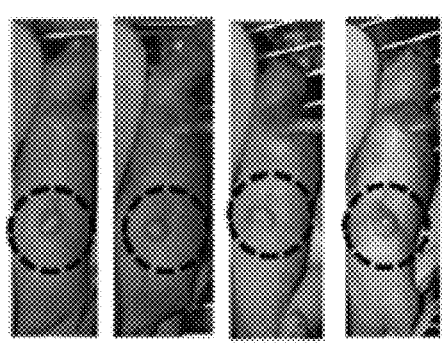
1  #2  #3  #4  #5

SEQUENCE LISTING

```
<160> NUMBER OF SEQ ID NOS: 11

<210> SEQ ID NO 1
<211> LENGTH: 344
<212> TYPE: PRT
<213> ORGANISM: Homo saipens

<400> SEQUENCE: 1

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Val Pro
```

```
                   225                 230                 235                 240

Thr Ile Ser Pro Ser Lys Ala Asn Tyr Arg Pro Gly Glu Asn Leu Asn
                        245                 250                 255

Leu Ser Cys His Ala Ala Ser Asn Pro Pro Ala Gln Tyr Ser Trp Phe
                        260                 265                 270

Ile Asn Gly Thr Phe Gln Gln Ser Thr Gln Glu Leu Phe Ile Pro Asn
                        275                 280                 285

Ile Thr Val Asn Asn Ser Gly Ser Tyr Met Cys Gln Ala His Asn Ser
                        290                 295                 300

Ala Thr Gly Leu Asn Arg Thr Thr Val Thr Met Ile Thr Val Ser Gly
        305                 310                 315                 320

Ser Ala Pro Val Leu Ser Ala Val Ala Thr Val Gly Ile Thr Ile Gly
                        325                 330                 335

Val Leu Ala Arg Val Ala Leu Ile
                        340

<210> SEQ ID NO 2
        <211> LENGTH: 276
        <212> TYPE: PRT
        <213> ORGANISM: Artificial Sequence
        <220> FEATURE:
        <223> OTHER INFORMATION: Recombinant CD66c

<400> SEQUENCE: 2

Lys Leu Thr Ile Glu Ser Thr Pro Phe Asn Val Ala Glu Gly Lys Glu
        1               5                   10                  15

Val Leu Leu Leu Ala His Asn Leu Pro Gln Asn Arg Ile Gly Tyr Ser
                        20                  25                  30

Trp Tyr Lys Gly Glu Arg Val Asp Gly Asn Ser Leu Ile Val Gly Tyr
                        35                  40                  45

Val Ile Gly Thr Gln Gln Ala Thr Pro Gly Pro Ala Tyr Ser Gly Arg
                50                  55                  60

Glu Thr Ile Tyr Pro Asn Ala Ser Leu Leu Ile Gln Asn Val Thr Gln
        65                  70                  75                  80

Asn Asp Thr Gly Phe Tyr Thr Leu Gln Val Ile Lys Ser Asp Leu Val
                        85                  90                  95

Asn Glu Glu Ala Thr Gly Gln Phe His Val Tyr Pro Glu Leu Pro Lys
                        100                 105                 110

Pro Ser Ile Ser Ser Asn Asn Ser Asn Pro Val Glu Asp Lys Asp Ala
                        115                 120                 125

Val Ala Phe Thr Cys Glu Pro Glu Val Gln Asn Thr Thr Tyr Leu Trp
                        130                 135                 140

Trp Val Asn Gly Gln Ser Leu Pro Val Ser Pro Arg Leu Gln Leu Ser
        145                 150                 155                 160

Asn Gly Asn Met Thr Leu Thr Leu Leu Ser Val Lys Arg Asn Asp Ala
                        165                 170                 175

Gly Ser Tyr Glu Cys Glu Ile Gln Asn Pro Ala Ser Ala Asn Arg Ser
                        180                 185                 190

Asp Pro Val Thr Leu Asn Val Leu Tyr Gly Pro Asp Val Pro Thr Ile
                        195                 200                 205

Ser Pro Ser Lys Ala Asn Tyr Arg Pro Gly Glu Asn Leu Asn Leu Ser
                        210                 215                 220

Cys His Ala Ala Ser Asn Pro Pro Ala Gln Tyr Ser Trp Phe Ile Asn
        225                 230                 235                 240

Gly Thr Phe Gln Gln Ser Thr Gln Glu Leu Phe Ile Pro Asn Ile Thr
```

245                 250                 255
Val Asn Asn Ser Gly Ser Tyr Met Cys Gln Ala His Asn Ser Ala Thr
            260                 265                 270

Gly Leu Asn Arg
        275

<210> SEQ ID NO 3
<211> LENGTH: 27
<212> TYPE: DNA
<213> ORGANISM: Artificial Sequence
<220> FEATURE:
<223> OTHER INFORMATION: CD66c gene forward primer

<400> SEQUENCE: 3
aagcttaagc tcactattga atccacg                                    27

<210> SEQ ID NO 4
<211> LENGTH: 26
<212> TYPE: DNA
<213> ORGANISM: Artificial Sequence
<220> FEATURE:
<223> OTHER INFORMATION: CD66c gene reverse primer

<400> SEQUENCE: 4
gatatcagtg actgtggtcc tattga                                     26

<210> SEQ ID NO 5
<211> LENGTH: 27
<212> TYPE: DNA
<213> ORGANISM: Artificial Sequence
<220> FEATURE:
<223> OTHER INFORMATION: HuIgFc forward primer

<400> SEQUENCE: 5
gatatcgacg tcgagtccaa atcttgt                                    27

<210> SEQ ID NO 6
<211> LENGTH: 26
<212> TYPE: DNA
<213> ORGANISM: Artificial Sequence
<220> FEATURE:
<223> OTHER INFORMATION: HuIgFc reverse primer

<400> SEQUENCE: 6
ctcgagttta cccggagaca gggaga                                     26

<210> SEQ ID NO 7
<211> LENGTH: 19
<212> TYPE: PRT
<213> ORGANISM: Artificial Sequence
<220> FEATURE:
<223> OTHER INFORMATION: epitope of 8F5 monoclonal antibody

<400> SEQUENCE: 7

Arg Asn Asp Ala Gly Ser Tyr Glu Cys Glu Ile Gln Asn Pro Ala Ser
1               5                   10                  15

Ala Asn Arg

<210> SEQ ID NO 8
<211> LENGTH: 831
<212> TYPE: DNA
<213> ORGANISM: Artificial Sequence
<220> FEATURE:
<223> OTHER INFORMATION: CD66c cDNA-hydrophobic region

<400> SEQUENCE: 8

```
actattgaat ccacgccgtt caatgtcgca gaggggaagg aggttcttct actcgcccac    60
aacctgcccc agaatcgtat tggttacagc tggtacaaag gcgaaagagt ggatggcaac   120
agtctaattg taggatatgt aataggaact caacaagcta ccccaggggcc cgcatacagt   180
ggtcgagaga caatataccc caatgcatcc ctgctgatcc agaacgtcac ccagaatgac   240
acaggattct atacccctaca agtcataaag tcagatcttg tgaatgaaga agcaaccgga   300
cagttccatg tatacccgga gctgcccaag ccctccatct ccagcaacaa ctccaacccc   360
gtggaggaca aggatgctgt ggccttcacc tgtgaacctg aggttcagaa cacaacctac   420
ctgtggtggg taaatggtca gagcctcccg gtcagtccca ggctgcagct gtccaatggc   480
aacatgaccc tcactctact cagcgtcaaa aggaacgatg caggatccta tgaatgtgaa   540
atacagaacc cagcgagtgc caaccgcagt gacccagtca ccctgaatgt cctctatggc   600
ccagatggcc ccaccatttc cccctcaaag gccaattacc gtccagggga aaatctgaac   660
ctctcctgcc acgcagcctc taaccaccct gcacagtact cttggtttat caatgggacg   720
ttccagcaat ccacacaaga gctctttatc cccaacatca ctgtgaataa tagcggatcc   780
tatatgtgcc aagcccataa ctcagccact ggcctcaata ggaccacagt c            831
```

<210> SEQ ID NO 9
<211> LENGTH: 600
<212> TYPE: DNA
<213> ORGANISM: Artificial Sequence
<220> FEATURE:
<223> OTHER INFORMATION: CD66c mutant(BI /BHI)

<400> SEQUENCE: 9

```
aagcttaagc tcactattga atccacgccg ttcaatgtcg cagaggggaa ggaggttctt    60
ctactcgccc acaacctgcc ccagaatcgt attggttaca gctggtacaa aggcgaaaga   120
gtggatggca acagtctaat tgtaggatat gtaataggaa ctcaacaagc taccccaggg   180
cccgcataca gtggtcgaga gacaatatac cccaatgcat ccctgctgat ccagaacgtc   240
acccagaatg acacaggatt ctataccccta caagtcataa agtcagatct tgtgaatgaa   300
gaagcaaccg gacagttcca tgtatacccg gagctgccca gccctccat ctccagcaac   360
aactccaacc ccgtggagga caaggatgct gtggccttca cctgtgaacc tgaggttcag   420
aacacaacct acctgtggtg ggtaaatggt cagagcctcc cggtcagtcc caggctgcag   480
ctgtccaatg gcaacatgac cctcactcta ctcagcgtca aaaggaacga tgcaggatcc   540
tatatgtgcc aagcccataa ctcagccact ggcctcaata ggaccacagt cacggatatc   600
```

<210> SEQ ID NO 10
<211> LENGTH: 378
<212> TYPE: DNA
<213> ORGANISM: Artificial Sequence
<220> FEATURE:
<223> OTHER INFORMATION: CD66c mutant(HPK/HdIII/PstI/klenow)

<400> SEQUENCE: 10

```
aagctgctgt ccaatggcaa catgaccctc actctactca gcgtcaaaag gaacgatgca    60
ggatcctatg aatgtgaaat acagaaccca gcgagtgcca accgcagtga cccagtcacc   120
ctgaatgtcc tctatggccc agatgtcccc accatttccc cctcaaaggc caattaccgt   180
ccaggggaaa atctgaacct ctcctgccac gcagcctcca acccacctgc acagtactct   240
tggtttatca atgggacgtt ccagcaatcc acacaagagc tctttatccc caacatcact   300
```

```
gtgaataata gcggatccta tatgtgccaa gcccataact cagccactgg cctcaatagg      360
accacagtca cggatatc                                                    378

<210> SEQ ID NO 11
<211> LENGTH: 705
<212> TYPE: DNA
<213> ORGANISM: Artificial Sequence
<220> FEATURE:
<223> OTHER INFORMATION: Human immunoglobulin Fc region CH2-CH3

<400> SEQUENCE: 11
gacgtcgagt ccaaatcttg tgacaaaact cacacatgcc caccgtgccc agcacctgaa       60
ctcctggggg gaccgtcagt cttcctcttc cccccaaaac ccaaggacac cctcatgatc      120
tcccggaccc ctgaggtcac atgcgtggtg gtggacgtga gccacgaaga ccctgaggtc      180
aagttcagct ggtacgtgga cggcgtggag gtgcataatg ccaagacaaa gccgcgggag      240
gagcagtaca acagcacgta ccgtgtggtc agcgtcctca ccgtcctgca ccaggactgg      300
ctgaatggca aggagtacaa gtgcaaggtc tccaacaaag ccctcccagc ccccatcgag      360
aaaaccatct ccaaagccaa agggcagccc cgagaaccac aggtgtacac cctgccccca      420
tcccgagagg agatgaccaa gaaccaggtc agcctgacct gcctggtcaa aggcttctat      480
cccagcgaca tcgccgtgga gtgggagagc aatgggcagc cggagaacaa ctacaagacc      540
acgcctcccg tgctggactc cgacggctcc ttcttcctct atagcaagct caccgtggac      600
aagagcaggt ggcagcaggg gaacgtcttc tcatgctccg tgatgcatga ggctctgcac      660
aaccactaca cgcagaagag cctctccctg tctccgggta aatga                     705
```

COMPOSITION FOR PREVENTING OR TREATING LUNG CANCER COMPRISING ANTIBODY AGAINST CD66C AND CHEMOTHERAPEUTIC AGENT

CROSS REFERENCE TO RELATED APPLICATION

The present application claims the priority of Application Serial No. 10-2016-0031167, filed on Mar. 15, 2016, and contains all the contents of said applications as a reference.

FIELD OF THE INVENTION

The present invention relates to a composition for preventing or treating a lung cancer, comprising an anti-CD66c antibody specific to lung cancer and an antigen-binding fragment thereof, or a cell producing them, in combination with at least one chemical anti-cancer agent, or a method of treatment for a subject being susceptible a lung cancer or being diagnosed as a patient with a lung cancer by using an anti-CD66c antibody specific to lung cancer and an antigen-binding fragment thereof, or a cell producing them, in combination with at least one chemical anti-cancer agent.

BACKGROUND OF THE INVENTION

It is known that a 5-year survival rate of lung cancer exceeds 80% if the lung cancer was found early in IA stage (Mulshine, J. L. and Sullivan, D. C. Clinical practice. Lung cancer screening. N. Engl. J. Med. 2005; 352:2714-2720). It is therefore important to find good markers that enables early discovery of lung cancer in pursuit of specific biological markers. Especially, lung cancer is a representative heterogeneous tumor, and the response and the prognosis are different for a variety of treatments. Lung cancer can be divided into two major categories medically, small cell lung cancer and non-small cell lung cancers (NSCLC). Non-small cell lung cancers can be further divided into lung adenocarcinoma, squamous cell carcinoma and large cell carcinoma.

Meanwhile, CD66c is known as CEACAM6 (Carcinoembryonic antigen-related cell adhesion molecule 6) or NCA (non-specific cross-reacting glycoprotein antigen)-90 and has a higher concentration in the blood of lung cancer, pancreatic cancer, breast cancer, rectal cancer and hepatoma patients. The above CD66c is an important protein for cell adhesion and is involved in adhesion of endothelial cells activated by cytokine in case of neutrophils.

Also, normal cells destroy themselves if cell adhesion is prevented. This process is called anoikis. Tumor cells, however, are resistant to such anoikis and promote cancer outbreak and metastasis of cancer as a result. There is a report that the above CD66c prevents anoikis, and there also is a report that malignant phenotype changes in cancer cells by regulating the expression of CD66c. Also, when the protein expression is inhibited by silencing CD66c genes by using small interfering RNA, metastasis is inhibited by enhancement of anoikis in vivo. In conclusion, metastasis can be prevented by inhibiting the function of CD66c.

SUMMARY OF THE INVENTION

The present inventors found that the combination administration of anti-CD66c antibody and a chemical therapeutic agent provided a synergic anti-cancer activity and completed the present invention.

Therefore, an embodiment of the present invention is to provide a composition comprising for preventing or treating a lung cancer, comprising an anti-CD66c antibody specific to lung cancer and an antigen-binding fragment thereof, or a cell producing them, in combination with at least one chemical anti-cancer agent, as active ingredients.

Another embodiment of the present invention is to provide a kit for preventing or treating a cancer, including a first pharmaceutical composition containing a therapeutically effective amount of anti-CD66c, a second pharmaceutical composition containing a therapeutically effective amount of a chemical therapeutic agent, and a packing vessel.

Further embodiment of the present invention is to provide a method of treatment for a subject being susceptible a lung cancer or being diagnosed as a patient with a lung cancer by using an anti-CD66c antibody specific to lung cancer and an antigen-binding fragment thereof, or a cell producing them, in combination with at least one chemical anti-cancer agent.

BRIEF DESCRIPTION OF THE DRAWINGS

FIG. 1 is a drawing representing the result of setting up the recombinant region of CD66c.

FIG. 4 is a result of confirming the expression of CD66c-HuIgFc recombinant antigen in transgenic CHO-K1 cell line by performing ELISA.

FIG. 14 is a result of confirming the epitope of monoclonal antibody of the present invention by performing MALDI-TOF.

FIG. 17 is a schematic to compare the epitope of the present invention elucidated by MOLDI-TOF and the verification results of the same.

FIG. 21 illustrates the increased chemical sensitivity of paclitaxel caused by treating 8F5 monoclonal antibody in a dose-dependent manner according to Example 6.

FIGS. 25a and 25b show the increased anti-cancer activity in case of the combination therapy of anti-CD66c monoclonal antibody with paclitaxel in xenograft mice model with A549 cell, according to Example 6.

DETAILED DESCRIPTION OF THE EMBODIMENTS

Figure 2:
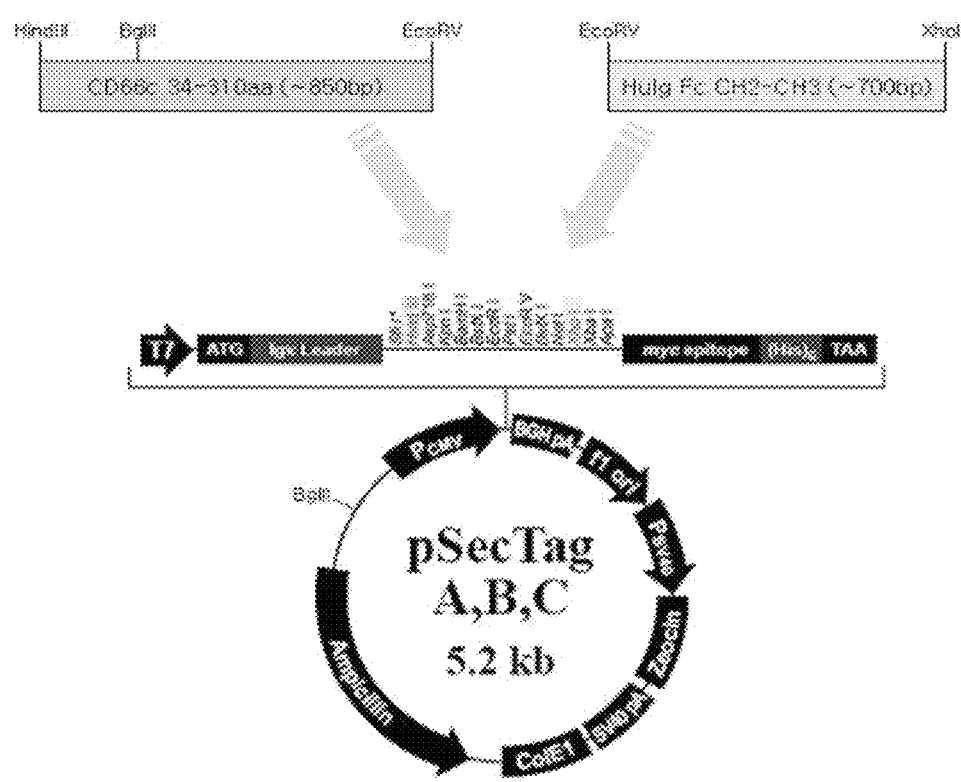
FIG. 2 is a schematic of designing pSegTag-CD66c-HuIgFc cloning.

A target-specific anticancer drug such as an antibody is more likely to have an acquired resistance than target-nonspecific anticancer drug. The efficacy of the anticancer drug can be maximized by inhibiting the factors causing the resistance in order to prevent the resistance of the target specific anticancer drug. In addition, the target-specific anticancer drugs have limited applications, and thus can be applied for more various applications by administering the target-specific anticancer drug with an inhibitor of other factors causing the resistance, When the target-specific anticancer drug has an efficacy as well as the resistance, an used amount of drug can be reduced by increasing the efficacy through the combination therapy. Thus, the efficacy of drug can be increased with minimizing the toxicity of the drug in the organ or tissue.

The present invention provides a combination therapy of an antibody specific to CD66c and other effective drug. In this combination therapy, the efficacy of anti-CD66c antibody can be increased as well as the synergic effect of combination therapy, and the amount of anti-CD66c antibody and/or a chemical therapeutic agent can be reduced. The reduced amount of administered anti-CD66c antibody and/or a chemical therapeutic agent can minimize the side effect, but maximize the anti-cancer activity. In addition, the combination therapy can provide enhanced anti-cancer activity of anti-CD66c antibody in the tumor or cancer lesion that the anti-CD66c antibody has no or little anti-cancer activity when it is used alone, and resolve the problem of resistance.

More particularly, the present invention relates to combination therapy of anti-CD66c antibody and a chemical therapeutic agent (chemotherapeutic agent). The pharmaceutical composition for the combination therapy can be a mixture of a chemotherapeutic agent and anti-CD66c antibody or an antigen-binding fragment thereof, or can be administrated simultaneously or sequentially in each formulation of chemotherapeutic agent and anti-CD66c antibody or an antigen-binding fragment thereof.

Cluster of Differentiation 66c (CD66c) is a protein known as carcinoembryonic antigen-related cell adhesion molecule 6 (CEACAM 6) or non-specific cross-reacting glycoprotein antigen (NCA)-90 and as an important protein for cell adhesion. CD66c can be represented preferably, but not limited to, amino acid sequence of SEQ ID No: 1 (Genebank Protein No. AAH05008).

An epitope in the present invention is a conformational determinants of an antigen is preferably, but not limited to, a linear epitope. The present invention provides a polypeptide of an epitope of CD66c (Cluster of Differentiation 66c) which is represented by the amino acid sequence of SEQ ID NO: 7.

In addition, an antibody or its antigen-binding fragment recognizing the polypeptide as an epitope can be provided. The present invention provides a cell line producing the antibody or its antigen-binding fragment An antibody in the present invention is a polypeptide or its fragment containing the framework region from the immunoglobulin gene, and an antibody specifically binds to and recognizes its antigen. Recognized immunoglobulin gene includes a recognized immunoglobulin gene includes kappa, lambda, alpha, gamma, delta, epsilon and mu conserved region in gene sequence and a variety of variable region in gene sequence. A light chain can be divided into kappa and lambda. A heavy chain can be divided into gamma, mu, alpha, delta or epsilon, and defined as immunoglobulin class IgG, IgM, IgA, IgD and IgE, respectively. Especially the antibody in the present invention includes chimeric and humanized antibodies.

The chimeric antibody in the present invention is an antibody that the sequence in the variable region is from one species and the sequence in the conserved region is from other species; for example, the variable region is from mouse and the sequence in the conserved region is from human.

The humanized antibody in the present invention is an antibody with low immunogenicity and with activity of non-human antibody. It can be prepared by keeping non-human CDR region and substitute the rest of the region with human counterparts. For example, the below literature is referenced: Morrison et al, Proc. Natl. Acad. ScL USA, 81:6851-6855 (1984); Morrison and Oi, Adv. Immunol., 44:65-92 (1988); Verhoeyen et al, Science, 239:1534-1536 (1988); Padlan, Molec. Immun., 28:489-498 (1991); Padlan, Molec. Immun., 31(3):169-217 (1994).

The antibody fragment in the present invention is not limited if it recognizes specifically CD66c epitope including variable region of a light chain ($V_L$) and variable region of a heavy chain ($V_H$), but can be selected from a group containing Fab, Fab', F(ab')2, scFv, dsFv and CDR. Especially, the scFv is an antibody fragment prepared as a single chain by connecting the variable region of a heavy chain ($V_H$) and variable region of a light chain ($V_L$) with a linker polypeptide The monoclonal antibody in the present invention is a terminology ordinary in the art, and is a highly specific antibody to a single antigen region. Conventionally unlike polyclonal antibody that includes different antibodies directed to different epitope, a monoclonal antibody is directed to a single epitope. The monoclonal antibody of the present invention can be prepared by conventional cloning or cell fusion technologies. For instance, natural or human monoclonal antibody can be produced by administrating antigen of the interest into a wild type or transgenic mice (BALB/c for example). Such antigen be administered alone or after mixing it with adjuvant, or expressed from a vector and immune response can be induced by DNA or fusion proteins. A fusion protein include intended peptide and coupled carrier peptide with immune response, for instance β-galactosidase, glutathione-S-transferase, keyhole limpet hemocyanin (KLH) and bovine serum albumin, and carrier proteins are not limited to them. In the above case, the peptide acts as hapten to the carrier protein.

Preparation method of the above monoclonal antibody can be explained as follows. After boosting an animal, spleen is removed to extract spleen cells and fused with myeloma cells by using publicly known technology in the art [Kohler and Milstein, Nature 256: 495-497 (1975); and Harlow and Lane, Antibodies: A Laboratory Manual, Cold Spring Harbor Laboratory, New York (1988)]]. Acquired hybridoma cells are cloned by limiting dilution, and acquired clones producing monoclonal antibody are cultured.

The monoclonal antibody has an advantage to improve the selectivity and specificity in diagnosis and analysis using antigen-antibody interactions and not to contaminate by other immunoglobulin since it is synthesized by hybridoma cultivation.

The hybridoma cell in the present invention is well known in the art, and is a cell formed by antibody producing cells and immortalized cells, for instance myeloma cells. The above hybridoma cell can produce antibodies continuously.

The polyclonal antibody in the present invention can be produced by injecting antigens including the epitope of the present invention, and preferably a portion of CD66c of SEQ ID No: 2 into an animal and draw blood to collect serum containing the antibody. Such polyclonal antibody can be purified by any of the methods known in the art, and can be prepared from a host of a goat, a rabbit, a sheep, a monkey, a horse, a pig, a cow and a dog.

The isolated polypeptide discovered to be an epitope of CD66c has a characteristic to be represented as amino acid sequence of SEQ ID No: 7.

The above epitope of CD66c is not limited to but preferably specific to lung adenocarcinoma.

In the embodiment of the present invention, the monoclonal antibody for CD66c specific to lung adenocarcinoma is developed (refer to Example 2) by immunizing lung adenocarcinoma cell line with CD66c recombinant antigens (refer to Example 1), and it is found for the first time that its epitope is amino acid sequence of SEQ ID No: 7 (refer to Example 3). Especially, the epitope of CD66c of the present invention is an epitope recognized specifically by monoclonal antibody (8F5) of the present invention unlike the conventional antibodies for CD66c, 9A6 (Santa Cruz biotechnology) or AP11 (DiNonA) (refer to Example 3).

Therefore, the epitope of CD66c represented by amino acid sequence of SEQ ID: 7 of the present invention can be used as an effective ingredient of an immunogenic composition to induce the formation of the antibody specific to lung adenocarcinoma.

The above epitope for CD66c can be separated from biological specimens, synthesized chemically, or produced by genetic engineering, and the above methods can be carried out easily by prior technologies.

Meanwhile, the antibody or its fragment of the present invention has a characteristic of recognizing the epitope of the present invention.

The antibodies of the present invention may be not limited thereto and preferably a monoclonal antibody or a polyclonal antibody. The monoclonal antibody may include variable region of a heavy chain and variable region of a light chain produced by the hybridoma cell deposited as an accession number: KCLRF-BP-00230, or may include a heavy chain and a light chain of an antibody produced by the hybridoma cell.

Especially, the antibody of the present invention is, not limited to, but preferably IgG1 and categorized to include kappa light chain (refer to Example 2-2).

The antibody of the present invention is not limited to, but preferably an antibody specific to lung adenocarcinoma.

In the embodiment of the present invention, the antibody of the present invention is developed by immunizing lung adenocarcinoma cell line with recombinant antigen of a region of CD66c represented by SEQ ID No: 2 and Fc of human immunoglobulin G, and by screening antibody specific to the above antigen in order to prepare antibody specific to lung adenocarcinoma (refer to Example 2-2).

We tested the hypothesis that a mAb binding to CEACAM6 could increase anoikis sensitivity by decreasing Akt phosphorylation, as observed in silencing of CEACAM6 gene. To this aim, we have established clone 8F5 mAb recognizing CEACAM6 by immunizing A549 lung adenocarcinoma cells and screening hybridoma clones that are double positive for A549 and CEACAM6-Fc. We explored the potential of clone 8F5 as a therapeutic mAb against lung adenocarcinoma and evaluated its mechanism for tumor growth inhibition. Our results demonstrate its potential benefit in combating lung adenocarcinoma, which is further enhanced by combined therapy with paclitaxel, by markedly inhibiting tumor growth in A549 xenograft model.

Meanwhile the cell line in the present invention has a characteristic of producing the above antibody or its fragments.

The above cell line is not limited to, but preferably to be hybridoma cells of deposition number KCLRF-BP-00230. The above hybridoma cell is a cell producing the above monoclonal antibody with its preparation method is well known in the field, and preferably can be produced by fusion between antibody producing cells and immortalized cells, for instance, myeloma cells. It can be prepared by cell fusion between preferably, but not limited to, myeloma cells (preferably X63-Ag8.653 cells) and mouse spleen cells immunized with lung adenocarcinoma cell line.

The above hybridoma cells are deposited as '8F5' to Korean Cell Line Research Foundation (KCLRF) on Feb. 22, 2010 with a deposition number KCLRF-BP-00230.

Meanwhile the diagnostic composition in the present invention has a characteristic of comprising the above antibody or its fragments.

The above antibody or antibody fragment specific to lung adenocarcinoma recognizes specifically the epitope of Cluster of Differentiation 66c (CD66c) represented by amino acid sequence of SEQ ID No: 7, detects CD66c antigen efficiently, and especially detect lung adenocarcinoma expressing CD66c antigen (refer to Example 4).

The antibody or its fragment specific to lung adenocarcinoma of the present invention has a superior inhibitory activity against cancer, especially lung adenocarcinoma (refer to Example 5).

Therefore, the pharmaceutical composition of the present invention can be used for the prevention or treatment of lung adenocarcinoma effectively by containing the above antibody or its fragment specific to lung adenocarcinoma.

The prevention and/or treatment effects for the cancer include as suppressing effect of cancer deterioration such as the inhibition of migration, invasion and/or metastasis of the cancer cells, as well as a suppressing effect of the cancer cell growth as well An antibody derived from animal which can be produced by immunizing the animal with antigen can cause immune rejection, when administered to human. The chimeric antibody has been developed for suppressing immune rejection.

The chimeric antibodies have been made by substituting the constant region causing anti-isotype reaction of animal-produced antibody with that of human antibody according to the biotechnological method. Although the chimeric antibodies have been improved anti-isotype reaction more than animal-derived antibody, but have potential side effect of the anti-idiotypic reaction because animal-derived amino acids remains in the variable region of the antibody. The humanized antibody has been developed for improving the side effects where complementarity determining regions (CDRs) playing important role in antigen binding of the chimeric antibody is transplanted into the framework of human antibody.

The most important technology in the CDR grafting for making a humanized antibody is selecting the optimized human antibody being capable of accepting the animal-derived CDR. To do this, antibody database, crystal structure analysis and molecular modeling technology are utilized. However, even if animal-derived CDRs are transplanted into optimized human antibody framework, the produced humanized antibody cannot conserve the antigen binding activity, because an amino acid locate at the framework of animal-derived antibody influences the antigen binding activity. Thus, it is essential for the additional antibody engineering to be applied for restoring the antigen binding activity.

According to one embodiment, the antibody may be mouse-derived antibody, mouse-human chimeric antibody, humanized antibody or human-derived antibody. The antibody or its antigen binding fragment may not be in nature, nor isolated from a living body. Also, the antibody or its antigen binding fragment may be produced with recombination or synthetic method.

The lung cancer according to the present invention includes lung adenocarcinoma, squamous cell carcinoma, large cell carcinoma, or small cell lung cancer.

The anticancer chemotherapeutic agent can be used in combination with an anti-CD66c antibody specific to lung cancer, its fragment, and/or a cell line producing the antibody. For example, the anticancer chemotherapeutic agent may be at least one selected from the group consisting of metabolic antagonists such as ALIMTA (pemetrexed) or GEMZAR (gemcitabine); real derivative compounds such as Taxol (paclitaxel), Taxotere (docetaxel) or etoposide; alkylation agent such as cisplatin or carboplatin; and a targeting cancer drugs such as IRESSA (gefitinib), Tarceba (erlotinib) or AVASTIN (bevacizumab).

The term, "prevention" used herein refers to all activities that inhibit or delay the onset of cancer by administrating a composition of the present invention. The term "treatment" refers to all activities that inhibit or delay the cancer aggravation by administrating a composition of the present invention and recover from cancer.

The pharmaceutical composition of the present invention may be used as single formulation, and a combined formulation including an additional medication with an approved—cancer treatment effect.

The term "pharmaceutically acceptable" means that it does not significantly stimulate an organism and inhibit the biological activity and properties of the administered active substances.

The content of the above antibody or its fragment as an active ingredient in the pharmaceutical composition of the present invention can be adjusted depending on the usage type, objective, patient condition, symptomatic type and heaviness of disease, and preferably 0.1~50 weight %, more preferably 1~20 weight %, but not limited to the range.

The pharmaceutical composition of the present invention can be administered to mammals including human via a variety of routes. Any conventionally methods of administration can be used, for instance, oral, rectal, intravenous, intramuscular, subcutaneous, intraepidural or intracerebroventricular administrations can be used.

The pharmaceutical composition of the present invention can be formulated by conventional methods into oral formulations such as powders, granules, tablets, capsules, suspensions, emulsions, syrup, aerosol or non-oral formulations such as transcutaneous formulation, Rectal Suppository and sterilized solution for injection.

The pharmaceutical composition of the present invention can contain adjuvant such as pharmaceutically acceptable and physiologically allowed carriers, excipients and diluents besides the above extracts. The carrier, excipients and diluents included in the pharmaceutical composition of the present invention can be lactose, dextrose, sucrose, sorbitol, mannitol, xylitol, erythritol, maltitol, starch, acacia gum, alginate, gelatin, calcium phosphate, calcium silicate, cellulose, methyl cellulose, amorphous cellulose, polyvinyl pyrrolidone, water, methylhydroxybenzoate, propylhydroxybenzoate, talc, magnesium stearate and mineral oil. In case of formulation, commonly used diluents or excipients such as fillers, extender, binder, humectant, disintegrant and surfactant can be used. Solid formulations for oral administration include tablets, pills, powder, granules and capsules, and can be prepared by mixing the above extract of Radix Polygalae Tenuifoliae, Rhizoma et Radix Ligustici and Arillus Euphoriae Longanae with one or more excipients such as starch, calcium carbonate, sucrose, lactose or gelatin. Also lubricants such as magnesium stearate and talc can be used instead of a simple excipients.

Liquid formulations for oral administrations include suspension, liquid and solution, emulsion, syrup, and frequently used water, liquid paraffin and other excipients such as humectant, sweetener, aromatics and preservatives can also be used. In the formulations for non-oral administration, sterilized aqueous solution, non-aqueous solvent, suspension, emulsion, freeze-dried formulation, rectal suppository and transcutaneous formulation are included. Propylene glycol, polyethylene glycol, vegetable oil, such as olive oil, and injectable esters, such as ethyloleate, can be used as non-aqueous solvent or suspension. The base for suppository includes witepsol, macrogol, tween 61, cacao oil, laurin oil, glycerol and gelatin.

The pharmaceutical composition of the present invention can be administered to human as a single formulation, but can also be administered by using general protocols or by mixing with pharmaceutical carriers selected in consideration of the standard pharmaceutical practice. For examples, the pharmaceutical composition of the present invention can be dose via oral, buccal or sublingual administration in the form of tablets containing starch or lactose, capsules alone or with excipients, or elixir or suspension with chemicals for taste masking or coloration. Such liquid formulations can be formulated with pharmaceutically acceptable additives such as suspensions (for instance methyl cellulose, semisynthetic glyceride such as witepsol, mixture of apricot kernel oil and PEG-6 esters, glyceride mixtures such as PEG-8 and caprylic/capric glyceride).

The administration dose of the pharmaceutical composition of the present invention can vary depending on the age, weight, health status and seriousness of the disease of the patient and administration type, and can be once or number of times a day at fixed time interval.

For instance, daily dose of the effective ingredient can be 1~20 mg/kg, and preferably 5~10 mg/kg. The above dose is only an average value, and the dose can be higher or lower depending on the personal differences. It is preferable to have the above dose range since meaningful effect cannot be obtained when the daily dose of the pharmaceutical composition of the present invention is lower than the above dose and it is not only uneconomical, but also can cause undesirable side-effects if the dose is higher.

In below, the present invention is explained by examples.

The following examples explain the present invention, but the present invention must not be restricted by these examples.

EXAMPLE 1

Preparation of Recombinant Antigen (CD66c-HuIgFc) by Linking CD66c and $C_H2$-$C_H3$, Human Immunoglobulin Fc Region <1-1> Gene Cloning In order to obtain CD66c-HuIgFc recombinant antigen, a primer for CD66c gene was prepared by defining 34~340 aa region (SEQ ID No: 2) designed by deleting hydrophobic region in CD66c whole cDNA (SEQ ID No: 1), and a primer for Human immunoglobulin Fc region $C_H2$-$C_H3$ (HuIgFc), specifically the base sequence represented by SEQ ID No: 11, was prepared (Table 1).

Schematic for whole cloning procedure is shown in FIG. 2.

TABLE 1

| Gene Primer | SEG ID | Sequence |
| --- | --- | --- |
| CD66cHnd66c 5' | SEG ID No: 3 | AAG CTT AAG CTC ACT ATT GAA TCC ACG |
| 66cEcRV 3' | SEG ID No: 4 | GAT ATC AGT GAC TGT GGT CCT ATT GA |
| HumanEcrVFc 5' Ig Fc | SEG ID No: 5 | GAT ATC GAC GTC GAG TCC AAA TCT TGT |
| (CH2-FcXhO1 3' CH3) | SEG ID No: 6 | CTC GAG TTT ACC CGG AGA CAG GGA GA |

The above CD66c gene was obtained by extracting RNA from human lung adenocarcinoma cell line, A549 (ATCC CCL-185) by using QIAGEN RNEasy Mini spin kit and performing RT-PCR by using primer shown in the above Table 1. Specifically, the above RT-PCR was performed with Novagen first cDNA synthesis kit, and more specifically by reacting RNA 1 ug and Oligo d(T) primer 1 µl (10 pmol/µl) at 70° C. for 10 min, cooling and reacting for 1 hour at 37° C. after adding 5× buffer, 100 mM DTT, reverse transcriptase to synthesize cDNA. The synthesized DNA was amplified by PCR using the primer in Table 1 with PCR premix (Bioneer, Korea) by performing 30 PCR cycles of 1 min at 94° C. and 2 min at 72° C. to obtain CD66c gene.

The result of the above experiment confirmed the 850 bp DNA of CD66c gene that can code the region of DNA in CD66c whole cDNA without the hydrophobic region (FIG. 3a), and the above DNA was cloned in pGEM T (Promega, USA) vector and confirmed by restriction enzyme, EcoRI, and sequenced to confirm the nucleic acid sequence of SEQ ID: 8.

Also the above Human Ig Fc region (HuIgFc) was obtained by extracting RNA using QIAGEN RNEasy Mini spin kit from human B cell (ATCC CTL-1834) and by performing the above RT-PCR using the primer in the above Table 1.

The above CD66c gene cloned pGEM T-CD66c gene was cleaved with HindIII and EcoRV restriction enzyme (Promega, USA) to prepare the insert, and HuIgFc was cleaved with EcoRV and XhoI to prepare two inserts. The pSegTagB (Invitrogen, USA) vector having Igk leader sequence as an expression vector was cleaved with restriction enzymes, HindIII and XhoI and two inserts were inserted simultaneously to complete the cloning.

Figure 3:
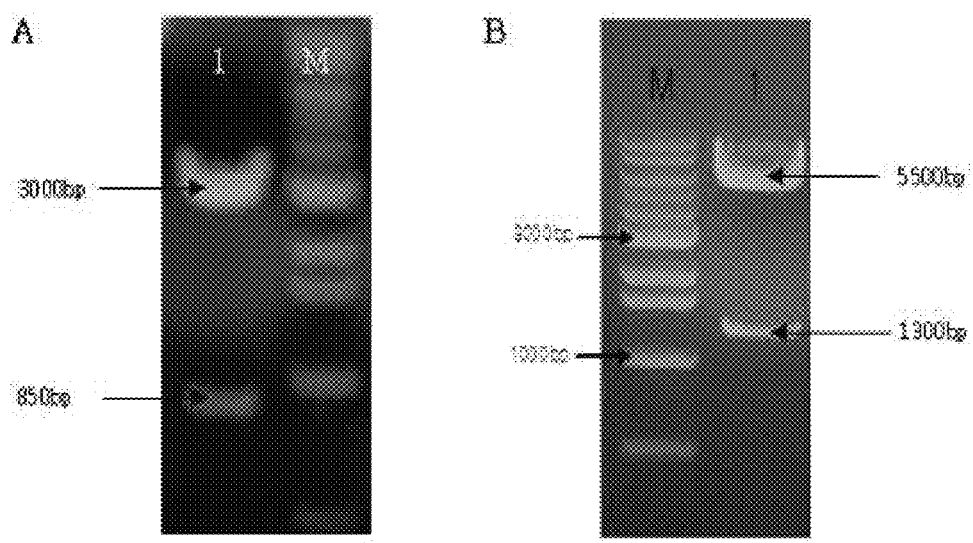
FIG. 3 is a result of confirming pSegTagB-CD66c-HuIgFc cloning.

Cloning of CD66c-HuIgFc recombinant DNA was confirmed by verifying the DNA fragment of 1300 bp by treating the final pSegTagB-CD66c-HuIgFc recombinant DNA with restriction enzyme BglII (FIG. 3b).

<1-2> Transfection and Establishment of Stable Cell Line

A cell line expressing recombinant antigen was developed by transfection of CHO-K1 cells (ATCC cells CRL-9618) with pSecTag-CD66c-HuIgFc DNA prepared in the above Example 1-1. Detailed experimental method is as follows.

Firstly, one day before the transfection, CHO-K1 cells were inoculated into 6-well plate at a concentration of $1\times10^6$ cells/ml and 3 ml of DMEM medium (Dulbecco's modified Eagle's medium, Gibco, USA) containing 10% Fetal bovine serum (Gibco, USA) was added and cultured for 18 hours at 37° C., under a 5% $CO_2$ condition. pSecTag-CD66c-HuIgFc DNA prepared in the above Example 1-1 was transfected to CHO-K1 cells using Effectene transfection reagent kit (QIAGEN, Hilden, Germany).

Three days after the above transfection, ELISA assay was performed for the supernatant using CD66c and HuIg to evaluate the amount of expressed CD66c-HuIgFc. To prepare stable cell line, selection process was performed using 150 ug/ml of Zeocin (Gibco, USA). After the selection process, single colony was obtained by performing limiting dilution) to establish the final cell line.

<1-3> Purification of Recombinant Antigen

In case of CD66c-HuIgFC recombinant antigen, it is easily expressed by applying Protein G-affinity chromatography to the supernatant of the cell line in the above Example 1-2 which expresses the antigen. Detailed experimental method is as follows.

Supernatant was collected after cultivating the stable cell line selected from the above Example 1-2, and was added with protein G-agarose (Thermo Fisher Scientific Inc. USA) and incubated at 4° C. overnight, and packed into a column and washed with 15 ml of washing buffer (20 mM Phosphate buffer, pH7.2). Afterwards, 5 ml of Elution Buffer (0.1M Glycine, pH 2.9) was added into the column to collect 1 ml fractions, which was neutralized by 100 µl of neutralizing buffer (1M TrisCl, pH 8.0) to obtain the purified CD66c-HuIgFc recombinant protein.

The recombinant protein obtained above was eluted after measuring the absorbance at 280 nm, and dialyzed with Phosphate buffered saline (PBS) solution. The concentration of the protein was determined by Protein Assay Kit (Thermo Fisher Scientific Inc. USA).

Figure 5:
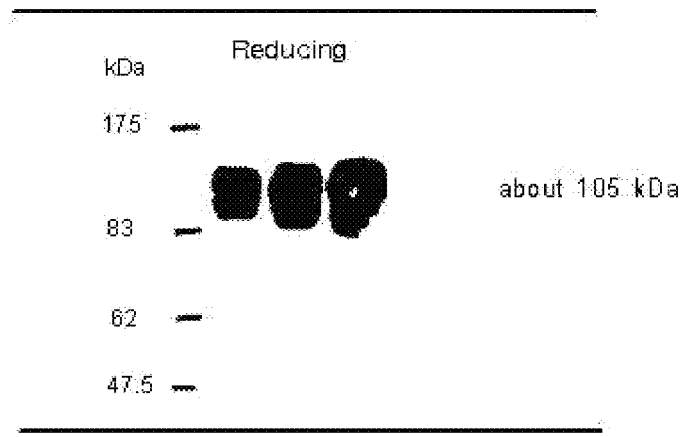
FIG. 5 is a western blot result confirming purified CD66c-HuIgFc recombinant antigens.

After loading 2, 5 and 10 µg of the purified antigen from the above protein G-affinity chromatography into a 10% Tris-glycine gel and transferred to nitrocellulose membrane, western blot was performed with human Ig-HRP to confirm the protein with molecular weight of 105 kDa (FIG. 5).

<1-4> Verification of Expression of Recombinant Antigen in Transformation Cell Line In order to verify the expression of CD66c-HuIgFc recombinant antigen in transfected CHO-K1 cell line in the above Example 1-2, three sandwich ELISA was performed by using AP11, an antibody of CD66c, and Goat anti-human Fc fragment and Goat anti-human Ig, antibodies of HuIgFc (refer to Table 2, mAb: monoclonal antibody)

TABLE 2

|  | method #1 | method #2 | method #3 |
|---|---|---|---|
| coating | anti-CD66c mAb (AP11) | anti-Human Ig Fc | anti-Human Ig |
| detecting | anti-Human Ig Fc-HRP | Mouse anti-CD66c mAb | |
|  |  | Goat anti-mouse IgM-HRP | |

Specifically 96-well micro titration plates (Maxisorp; Nunc, Roskilde, Denmark) were coated with 100 ng/well of AP11 mAb (DiNonA, Korea) and 400 ng/well of Goat anti-human Fc fragment, Goat anti-human Ig antibody, each diluted in PBS and incubated for 1 hour at 37° C. Afterwards, the reaction was blocked by adding 200 µl/well of 1× blocking buffer (blocking buffer, Sigma) and incubated for 1 hour at 37° C. One hundred microliters of the supernatant of transfected CHO-K1 cell line in the above Example 1-2 was added to each well to induce binding with the coated antibodies for 1 hour at 37° C., and the unconjugated antibody was removed by washing three times with PBS.

In the above well with conjugated AP11 mAb and supernatant, hydroperoxidase (HRP) conjugated goat anti-human Fc fragment specific Ab (Jackson Immuno Research Laboratories, West Grove, Pa.) was added and reacted for 30 min at 37° C., and in the well with conjugated anti-human Ig Fc, anti-human Ig and supernatant, mouse anti-CD66c mAb was added and reacted for 1 hour at 37° C. The cells were washed 3 times with PBS and added with HRP conjugated goat anti mouse IgM (Jackson Immuno Research Laboratories, West Grove, Pa.) and reacted for 30 min at 37° C. After binding HRP as above, the wells were washed with PBS to remove unconjugated HRP conjugate. After adding 50 µl/well substrate solution and reacted for 10 min at room temperature, the reaction was terminated with 2 N sulfuric acid. The progress of the reaction was monitored by measuring absorbance at 450 nm using ELISA reader, and the result is shown in FIG. 4. As a control group, cell supernatant obtained by transfection of pSegTag vector only and a different antigen, PD1 (DiNonA, Korea) conjugated with HuIgFc were used.

As shown in FIG. 4, CD66c-HuIgFc recombinant antigen is expressed in the transformed CHO-K1 cell line in the above Example 1-2.

<1-5> Verification of Function of Recombinant Antigen

Figure 6:
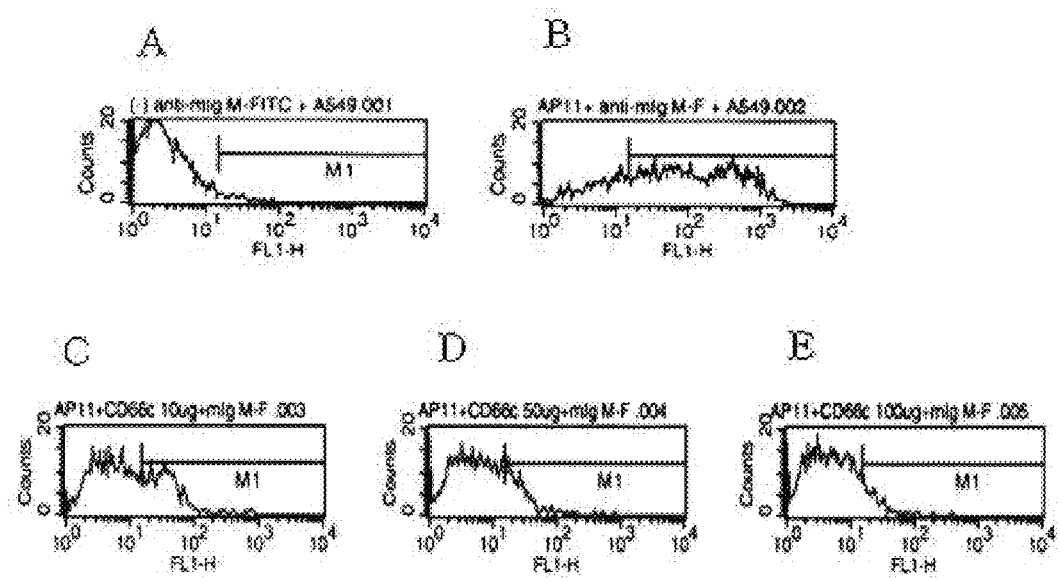
FIG. 6 is a result of confirming CD66c activity of recombinant CD66c-HuIgFc.

In order to confirm whether the purified recombinant antigen (CD66c-HuIgFc) in the above Example 1-3 acts as CD66c antigen, inhibition of conjugation of anti-CD66c antibody, AP11, on the surface of A549 cells by the above recombinant antigen was confirmed by flow cytometry, and the result is shown in FIG. 6.

Specifically, after conjugating 0, 10, 50 and 100 µg of the above recombinant antigen with AP11 antibody for 30 min at 4° C., it was added to A549 cells and reacted for 30 min at 4° C., added with 3 ml of PBS, centrifuged for 3 min at 1500 rpm and washed. To confirm the conjugated antibody, secondary antibody, goat anti-Mouse IgM FITC (DiNonA) was diluted 200 times, added, reacted for 15 min at 4° C., washed as above with 3 ml of PBS and measured by flow cytometry.

As shown in the above FIG. 6, positive result is observed for those without CD66c-HuIgFc (FIG. 6b), but blocking was observed proportional to the treated amount when the above recombinant antigen (CD66c-HuIgFc) was conjugated with 10, 50 and 100 µg of anti-CD66c mAb and conjugated subsequently with A549 cells (FIGS. 6c, d and e).

EXAMPLE 2

Development of Lung Adenocarcinoma Specific Monoclonal Antibody

<2-1> Preparation of Hybridoma Cell and Monoclonal Antibody

Figure 7:
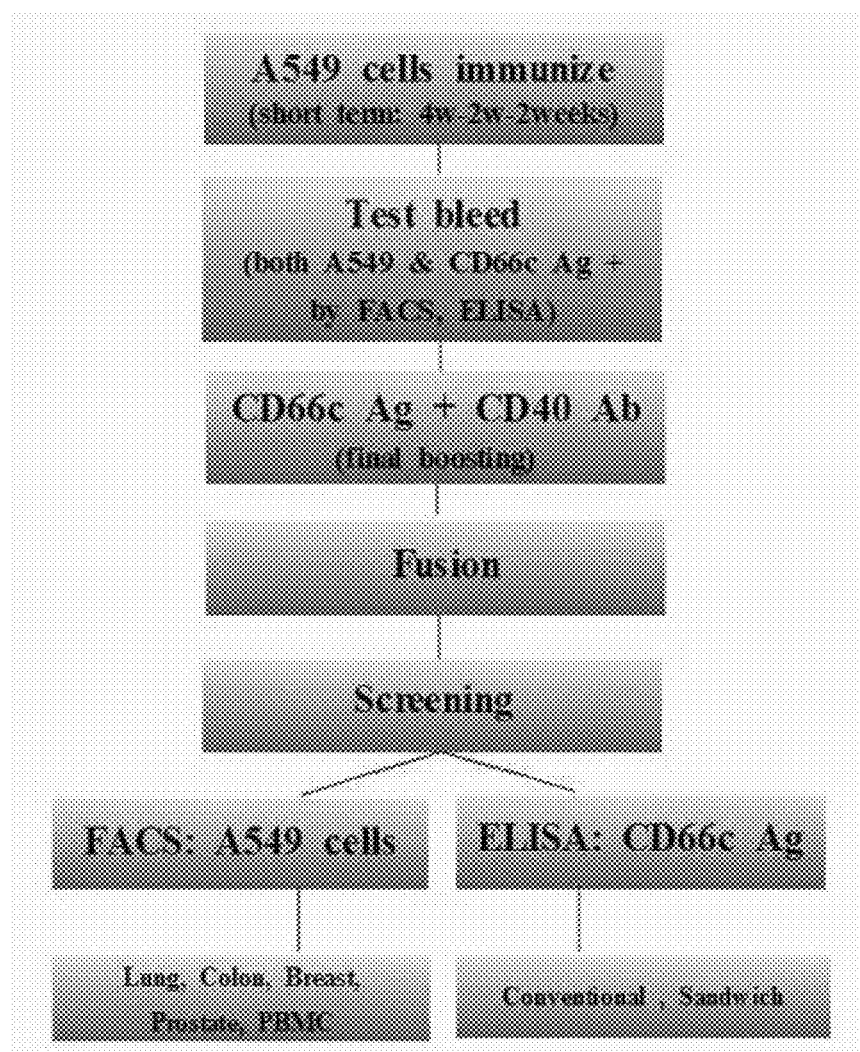
FIG. 7 is a schematic of developing monoclonal antibody for lung adenocarcinoma specific CD66c.

In order to develop monoclonal antibody specific to CD66c expressed in adenocarcinoma, adenocarcinoma A549 cell line was immunized instead of direct immunization of the above recombinant CD66c-HuIgFc, and the above recombinant CD66c-HuIgFc was injected at the boosting stage to amplify antibodies for CD66c. In the selection process of hybridoma, antibody which is positive for both CD66c-HuIgFc and A549 cell was selected to obtain antibody for CD66c expressed in adenocarcinoma (refer to FIG. 7).

Figure 8:
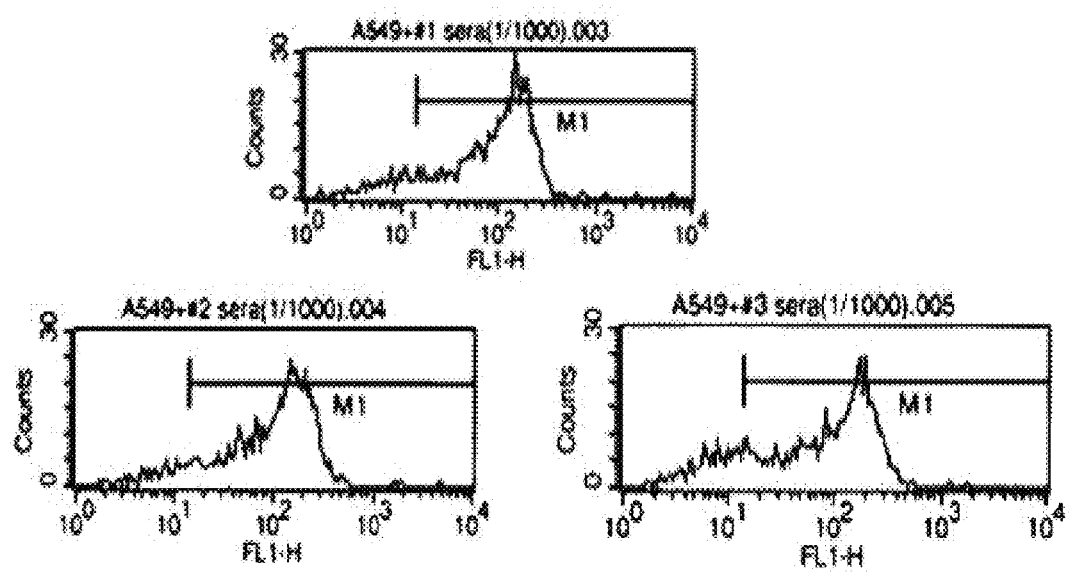
FIG. 8 is a result of confirming titers for A549 cells in the serum of A549 immunized mice.
Figure 9:
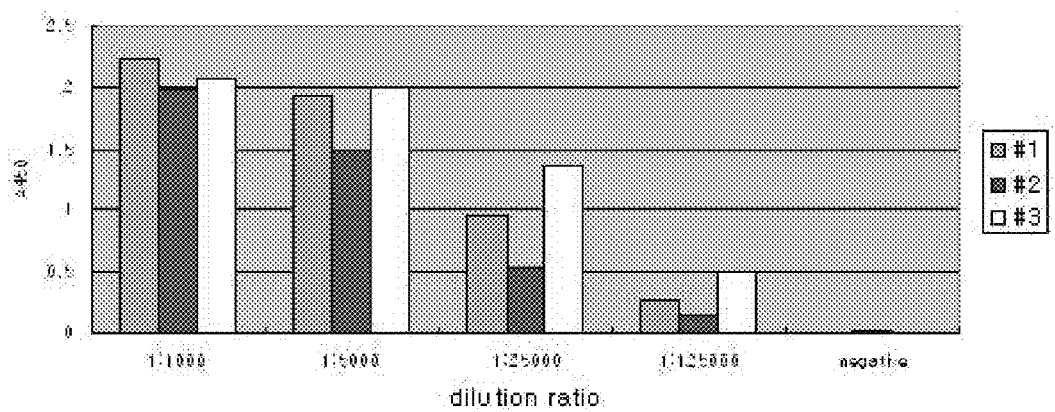
FIG. 9 is a result of confirming titers for CD66c-HuIgFcd in the serum of A549 immunized mice.

In order to develop adenocarcinoma specific monoclonal antibody, $1 \times 10^7$/mouse A549 cells (ATCC CCL-185), adenocarcinoma cell line, was injected into the intraperitoneal cavity of a 6-week old female Balb/c mouse three times in 3-week intervals. Blood samples were obtained from the tail vein to collect the serum. In the above separated serum, purified CD66c-HuIgFc in the above Example 1 was added, reacted for 1 hour at 37° C. for coating and terminated by of adding 200 µl/well of the blocking buffer (sigma). In the coated plate, separated serum was added after dilution, reacted for 1 hour at 37° C., and washed with PBS to remove unconjugated antibody. In order to identify conjugated antibody, secondary antibody, goat anti-Mouse Ig-HRP (Jackson) was diluted by 200 times and added at 100 µl/well, reacted at 37° C., and washed with PBS. After adding 50 µl/well of TMB (3, 3', 5, 5'-tetramethylbenzidene) substrate solution and reacted for 10 min at room temperature, the reaction was terminated with 2 N sulfuric acid (Sigma). The titer was confirmed by measuring absorbance at 450 nm using ELISA reader. Diluted serum was added to A549 cells, reacted for 30 min at 4° C., washed with 3 ml of PBS, centrifuged for 3 min at 1500 rpm, and washed to remove unconjugated antibody. In order to identify conjugated antibody, secondary antibody, goat anti-Mouse Ig-FITC(DiNonA) was diluted by 200 times and added, reacted for 15 min at 4° C., washed with 3 ml of PBS and measured with flow cytometry to confirm the titer for CD66c. The results are shown in FIGS. 8 and 9. Specifically, 3 day before the cell fusion, immune response was amplified by adding 50 µg of anti-CD40 agonist mAb and injected with 100 µg of CD66c-HuIgFc to induce the amplification of antibody for CD66c.

As shown in the above FIGS. 8 and 9, the titers for A549 cells are high for all as verified by flow cytometry (FIG. 8), and positive response for CD66c-HuIgFc was high in the A549 cell-immunized serum even though the CD66c antigen is not directly immunized (FIG. 9).

After obtaining single cell suspension from the incised spleen from the above immunized mice, the cells were washed twice with RPMI (GIBCO), and mixed with 0.4% trypan blue (sigma). The number of cells was counted by trypan blue assay that counts unstained cells by microscope. SP2/0 (ATCC CRL-1581) or X63 moue myeloma cell line (ATCC CRL-1580) was used as partner cells for cell fusion, and was counted like the above spleen cells, washed and counted.

The above myeloma cells and spleen cells were mixed in 1:5 ratios, and centrifuged to remove the supernatant. One milliliter of 50% of polyethylene glycol 1500 preheated to 37° C. was added slowly. After 1 min delay, RPMI medium was added slowly and diluted sequentially. After centrifugation, cells were suspended in RPMI (20% FBS, hypoxanthine-aminopterin-thymidine) supplemented with 1×HAT, and 100 μl/well of aliquots were added into 96-well plate and cultured in 5% $CO_2$ incubator at 37° C. After the above fusion, HAT feeding was progressed for a certain period of time, and when wells with colony formation was observed, 100 μl of the supernatant is added to A549 cell, adenocarcinoma cell line, reacted for 30 min at 4° C., added with 3 ml of PBS, and centrifuged for 3 min at 1500 rpm to remove unconjugated antibody. In order to confirm conjugated antibody, secondary antibody, goat anti-Mouse Ig-FITC (DiNonA) was added after a 200-fold dilution, reacted for 15 min at 4° C., washed with 3 ml of PBS as above and measured by flow cytometry. Purified CD66c-HuIgFc using CD66c-HuIgFc was added at 100 ng/well, coated by reacting for 1 hour at 37° C., and terminated by adding blocking buffer (sigma) at 200 μl/well and reacting for 1 hour at 37° C. In the coated plate, 100 μl/well of hybridoma supernatant was added and reacted for 1 hour at 37° C., and the unconjugated antibody was washed with PBS. Finally, to confirm the conjugated antibody, secondary antibody, goat anti-Mouse Ig-HRP (Jackson) was diluted by 200 times and added at 100 μl/well, and reacted at 37° C. and washed with PBS. After adding 50 μl/well of TMB (3, 3', 5, 5'-tetramethylbenzidene) and reacting for 10 min at room temperature, the reaction was terminated with 2 N sulfuric acid (Sigma). The result was monitored by measuring absorbance at 450 nm to perform enzyme-linked immunosorbent assay (ELISA).

The 8F5 monoclonal antibody showing positive in both of the above two methods was selected, and finally, the hybridoma cells expressing single colony 8F5 mAb was obtained through limiting dilution.

<2-2> Isotype Determination of Monoclonal Antibody

In order to determine the isotype of 8F5 monoclonal antibody prepared in the above Example 2-1, analysis was performed with mouse immunoglobulin isotyping ELISA kit (BD Biosciences, USA). Specifically, isotyping was performed with rabbit anti-murine isotype specific antisera (IgG1, IgG2a, IgG2b, IgG3, IgM, IgA, Kappa, Lambda) and peroxidase-labeled goat anti-rabbit IgG were used as secondary antibody. Color reaction was induced by using ortho-phenylenediamine (OPD) and hydrogen peroxide substrate and confirmed by measuring the absorbance at 450 nm.

The results confirmed that 8F5 monoclonal antibody is mouse IgG1/kappa light chain (data not shown).

<2-3> Detection of CD66c Antigen Using Monoclonal Antibody

Western blotting was performed for A549 cell lysate and recombinant antigen (CD66c-HuIgFc) by using 8F5 monoclonal antibody of the present invention and anti-CD66c AP11 antibody.

Specifically, after suspending $1 \times 10^7$ cells of adenocarcinoma cell line, A549 in 100 μl of lysis buffer (1% Nonidet P-40; NP-40 in 50 mM Tris-HCl, pH 7.4, 50 mM EDTA, and 1 mM phenyl-methyl-sulfonyl-fluoride; PMSF), cells were lysed for 15 min at room temperature and centrifuged to remove cell debris, and supernatant was collected to prepare the lysate. After boiling the prepared A549 lysate and recombinant antigen (CD66c-HuIgFc) obtained in the above Example 1 for 3 min, they were loaded to 8% sodium dodecyl sulfate-polyacrylamide gel electrophoresis (SDS-PAGE) under reducing and non-reducing conditions. After electrophoretic transfer onto a nitrocellulose membrane, reaction was blocked with 5% skim milk (sigma) and conjugated to 8F5 or AP11 monoclonal antibody. Those conjugated with 8F5 monoclonal antibody was washed 3 times with PBS and conjugated to peroxidase-conjugated goat anti-mouse IgG (Sigma, Saint Louis, USA). And those treated with AP11 monoclonal antibody was reacted with peroxidase-conjugated goat anti-mouse IgM (Sigma, Saint Louis, USA). After washing the above nitrocellulose membrane with PBS, bands were confirmed with enhanced chemiluminescence detection system (ECL, Amersham, Sweden), and the result is shown in FIG. 10.

Figure 10:
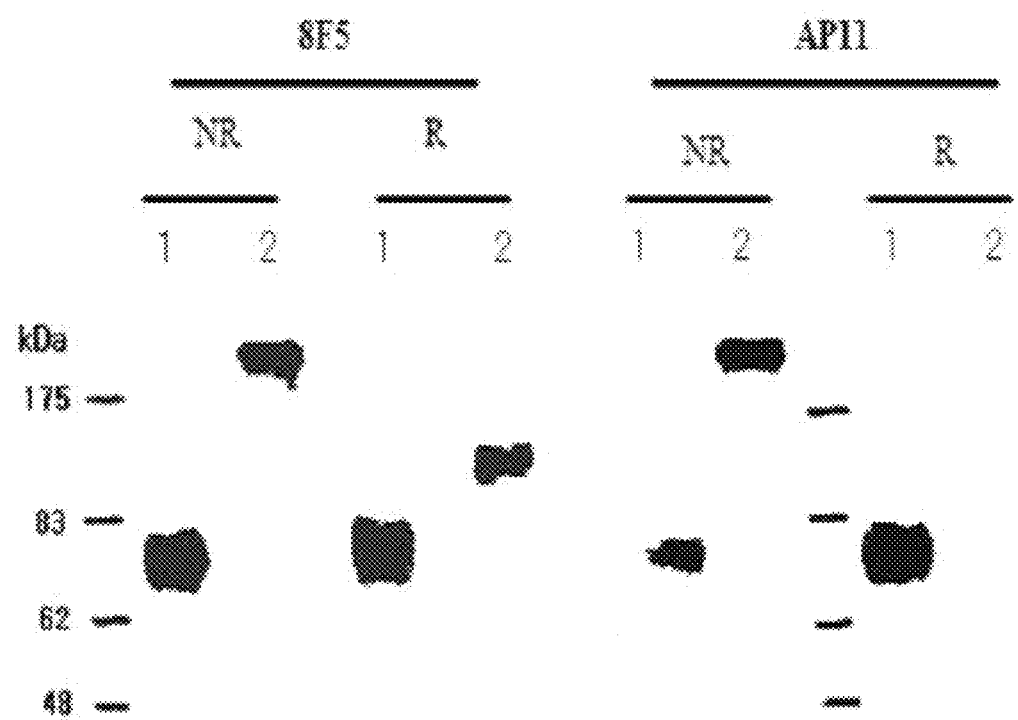
FIG. 10 is a result comparing the western blotting results between 8F5 and AP11.

As shown in FIG. 10, two antibodies were confirmed to show approximately 75 kDa band under non-reduced and reduced conditions. In case of recombinant CD66c-HuIgFc, band was confirmed at 210 kDa for both antibodies under non-reduced condition, and at 105 kDa under reduced condition. The reason for the difference in size for recombinant CD66c-HuIgFc was due to dimer formation in HuIgFc region, but not due to the difference in protein size.

In conclusion, the results of western blotting for the conventional anti-CD66c, AP11 and 8F5 coincide well. Therefore, it is shown that CD66c antigen can be detected by using monoclonal antibody of the present invention.

Meanwhile, CD66c antigen is known to be expressed in granulocytes in blood. Therefore, to confirm the degree of conjugation between peripheral blood and 8F5, after adding 1 μg of 8F5 antibody into peripheral blood mononuclear cells (Korean Red Cross blood centers) and reacted for 30 min at 4° C. and added with 3 ml of PBS, the product was centrifuged for 3 min and washed to remove unconjugated antibodies. In order to confirm conjugated antibody, secondary antibody, goat anti-Mouse Ig-FITC (DiNonA) was added after a 200-fold dilution, reacted for 15 min at 4° C., washed with 3 ml of PBS as above and measured by flow cytometry. The result is shown in FIG. 11.

Figure 11:
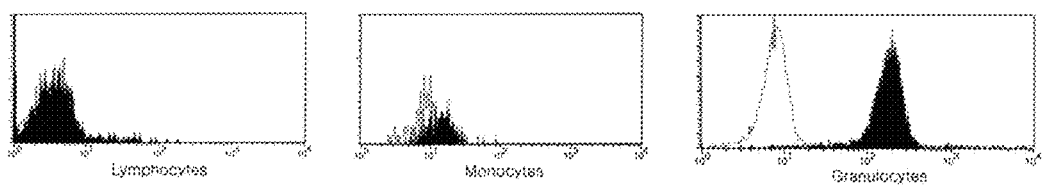
FIG. 11 is a result of the analysis to confirm the binding of 8F5 monoclonal antibody in peripheral blood mononuclear cells.

As shown in the above FIG. 11, CD66c antigen is shown to be expressed by using 8F5 monoclonal antibody in almost all granulocytes at 98% rate, but not in lymphocytes and monocytes.

Also, in order to confirm the conjugation between 8F5 and CD66c-HuIgFc using well-known 9A6 (Santa Cruz, USA) besides AP11 as a monoclonal antibody for anti-CD66c, purified CD66c-HuIgFc was added at 100 ng/well and reacted for 1 hour at 37° C. for coating and blocked by reacting with 200 μl/well of blocking buffer (sigma) 1 hour at 37° C.

In the coated plate, 100 μl/well of 9A6, 8F5 and AP11 antibodies were added and reacted for 1 hour at 37° C., and unconjugated antibody was washed with PBS. Finally, in order to confirm the conjugated antibody, 100 μl/well of the secondary antibody, goat anti-Mouse Ig-HRP (Jackson) was added after a 200-fold dilution, reacted at 37° C., washed with PBS. After adding 50 μl/well of TMB (3, 3', 5, 5'-tetramethylbenzidene) substrate solution and reacted for 10 min at room temperature, the reaction was terminated with 2 N sulfuric acid (Sigma). The result was monitored by measuring absorbance at 450 nm using ELISA reader, and is shown in FIG. 12.

Figure 12:
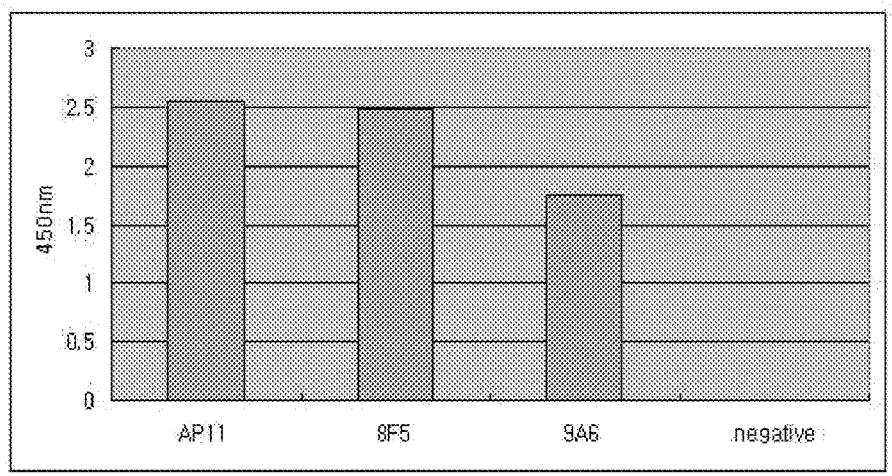
FIG. 12 is a result of ELISA analysis for CD66c-HuIgFc.

As shown in the above FIG. 12, all 3 antibodies have high values for CD66c-HuIgFc, but the activities of three clones are different.

<2-4> Analysis of Expression of CD66c Antigen in Lung Adenocarcinoma Cell Line Using 8F5 Monoclonal Antibody Binding of 8F5 monoclonal antibody to a variety of cancer cell lines obtained from KCLB (Korean Cell Line Bank) and SNU (Seoul National University) was confirmed by flow cytometry.

Specifically, cancer cell lines were obtained from Korean Cell Line Bank and Seoul National University. L-132, SW-900, DU145, LNCap, MDA-MB231 and MCF-7 were cultured in Dulbecco's MEM (GIBCO, Invitrogen) medium supplemented with 10% heat inactivated fetal bovine serum (FBS; GIBCO, Invitrogen) and A549, NCI-H460, NCI-H417, DLD-1, HCT116, HT-29, SW-480, SW-620 and PC-3 were cultured in RPMI 1640 (GIBCO, Invitrogen) medium supplemented with 10% heat inactivated FBS in an incubator at 37° C. under 5% $CO_2$ conditions.

After culturing the above cultured cancer cell lines by adding 8F5 monoclonal antibody of the present invention for 30 min at 4° C. and washing with PBS, FITC-conjugated goat anti-mouse Ig G (DiNonA Inc, Korea) was added for culture for 15 min at 4° C. After washing it again with PBS, the result was analyzed by FACSCalibur (Becton Dickinson, USA) and is shown in Table 3.

TABLE 3

| Cell line | Origin | Result |
| --- | --- | --- |
| L-132 | Lung normal | − |
| A549 | Lung adenocarcinoma | +++ |
| NCI-H460 | Squamos lung cancer | − |
| SW-900 | Large cell lung cancer | − |
| NCI-H417 | Small cell lung cancer | − |
| DLD-1 | Colon cancer | − |
| HCT116 | Colon cancer | − |
| HT-29 | Colon cancer | + |
| SW-480 | Colon cancer | − |
| SW-620 | Colon cancer | − |
| MDA-MB-231 | Breast cancer | − |
| MCF7 | Breast cancer | − |
| LNCap | Prostate cancer | − |
| Du-145 | Prostate cancer | − |
| PC-3 | Prostate cancer | − |

The percentage of 8F5 positive cells among 5000 cells were performed by FACS analysis
−: less than 10% of positive cells
+: 10~25%,
++: 25~50%,
+++: 50~75%,
++++: 75~90%

As shown in above Table 3, 8F5 monoclonal antibody of the present invention binds highly in adenocarcinoma cell line A549, but not at all in 4 colon cancer cell lines, 3 prostate cell lines, 2 breast cancer cell lines except for normal lung cell line, L-132 and small cell carcinoma cell line, NCI-H417 and weakly in colon cancer cell line, HT-29.

<2-5> Analysis of Expression of CD66c Antigen in Lung Cancer Tissues Using 8F5 Monoclonal Antibody Immunohistochemical staining for 8F5 was performed with the frozen tissues of normal thymus, lymph node, tonsil, spleen, kidney, urethra and skin obtained from Chungbuk National University Hospital. Clinical lung cancer tissues were fixed with 10% formalin (sigma) and embedded into paraffin.

Figure 13:
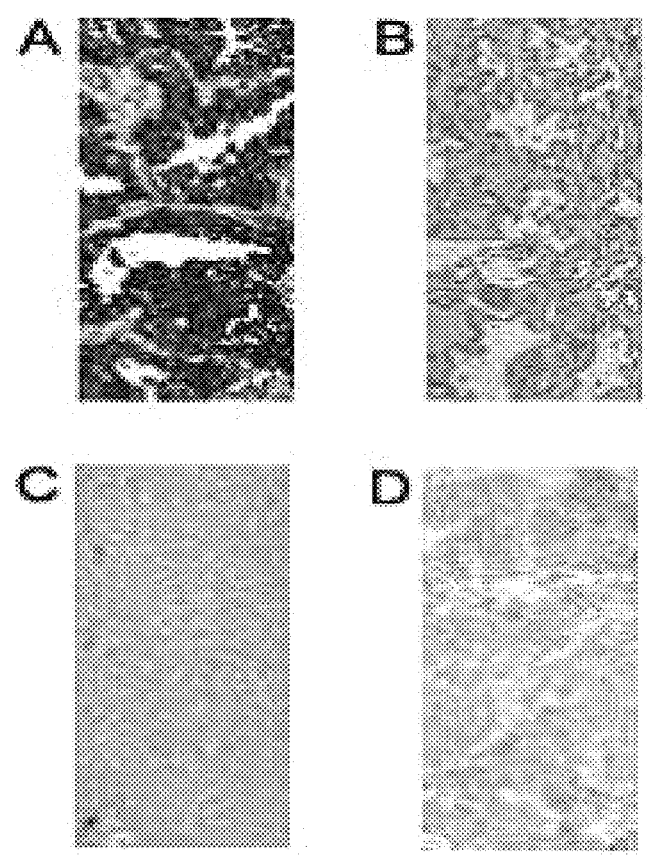
FIG. 13 is a result to confirm the 8F5 staining in lung cancer specimen.

Specifically, tissue staining was performed by adding 8F5 monoclonal antibody into blocking buffer (4% skim milk, 0.1% Tween-20, PBS), reacted overnight at 4° C., added with biotinylated goat anti-mouse IgG and HRP conjugated streptavidin (Dako, Denmark) for conjugation for 20 min at room temperature. Color reaction was performed by using 3,3'-diaminobenzidine (Sigma, Saint Louis. USA), and the results are shown in Table 4 and FIG. 13.

TABLE 4

|  | Tymus | Lymphnode | Tonsil | Spleen | Kidney | Urethra | Skin |
| --- | --- | --- | --- | --- | --- | --- | --- |
| Cortex | — | — | — | — | — | — | — |
| Medulla | — | — | — | — | — | — | — |
| B cell | — | — | — | — | — | — | — |
| T cell | — | — | — | — | — | — | — |
| Epithelium | — | — | — | — | — | — | — |
| Endothelium | — | — | — | — | — | — | — |
| Tubular | — | — | — | — | — | — | — |
| GM | — | — | — | — | — | — | — |
| GC | — | — | — | — | — | — | — |
| SE | — | — | — | — | — | — | — |
| ECC | — | — | — | — | — | — | — |
| KR | — | — | — | — | — | — | — |

Various human frozen tissues were stained by immunohistochemical method. All of them were not expressed.

As shown in the above Table 4, 8F5 monoclonal antibody staining is negative for all of the normal frozen tissues obtained through Chungbuk National University Hospital.

However, brown positive response was confirmed in the lung adenocarcinoma tissues (FIGS. 13a and b), and negative response was observed for squamous cell carcinoma tissue (FIG. 13c) and small cell carcinoma tissues (FIG. 13d) proving that 8F5 monoclonal antibody of the present invention can be used for the detection of lung adenocarcinoma tissue.

EXAMPLE 3

Epitope Determination of Monoclonal Antibody of the Present Invention

<3-1> Epitope Determination of Monoclonal Antibody of the Present Invention

In order to determine the epitope of 8F5 antibody, monoclonal antibody prepared in the above Example 2 of the present invention, protein peptide analysis using MALDI-TOF was utilized.

First, after adding 2 to 5 μg of the above 8F5 antibody and 20 μl of Protein A resin (Amersham Pharmacia) for binding for more than 12 hours at 4° C., 500 μl of A549 lysate was added and rotated for more than 4 hours at 4° C., and proteins that were not bound to antibody was removed by washing with PBS to obtain proteins bound to the antibody in protein A resin. Protein was loaded to SDS-PAGE gel to separate proteins, trypsinized and performed with MALDI- TOF (Mass spectrometric sequencing of proteins silver-stained polyacrylamide gels. Shevchenko A, Wilm M, Vorm O, Mann M. Anal Chem. 1996 Mar. 1; 68(5):850-8.) to analyze the peptides. The computer screen of the above analysis was captured in FIG. 14.

Figure 14:
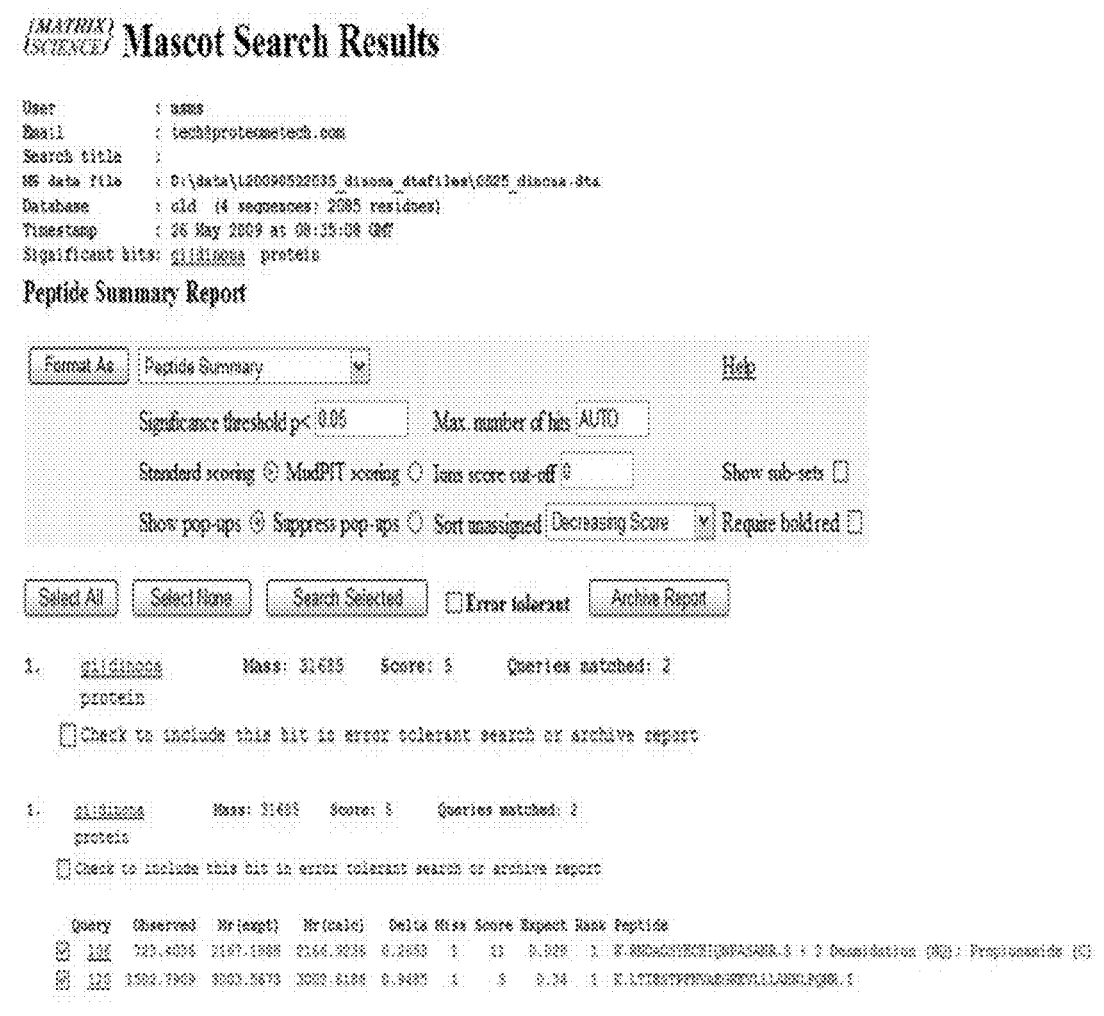

As shown in FIG. 14, the epitope of the monoclonal antibody of the present invention is represented by amino acid sequence of SEQ ID No: 7 (RNDAGSYECEIQN-PASANR).

<3-2> Epitope Verification of Monoclonal Antibody of the Present Invention

Figure 15:
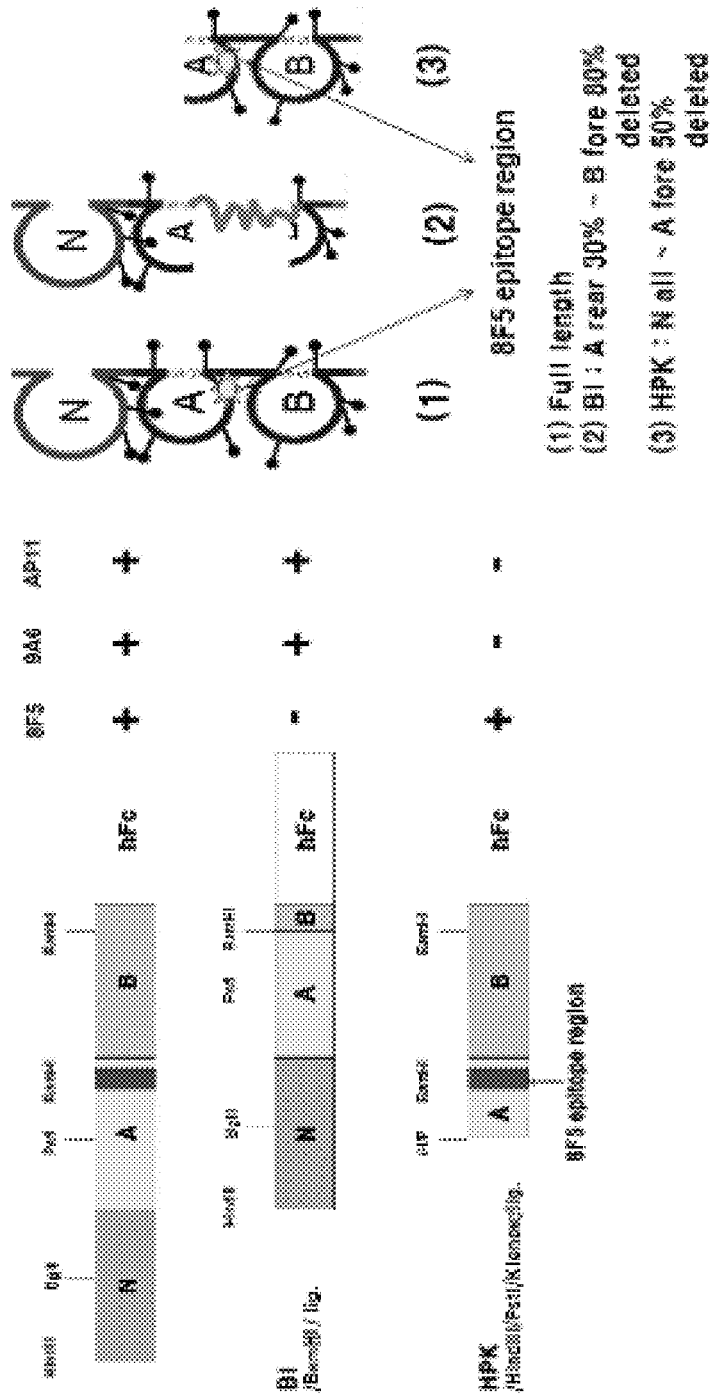
FIG. 15 is a schematic of the verification method of epitope of the monoclonal antibody of the present invention.

It was confirmed that antigen for 8F5 antibody is CD66c by the above proteomic analysis in the above Example 3-1. To verify its epitope, recombinant antigens with or without epitope region determined in the above Example 3-1 were prepared to evaluate the immune response for 8F5 antibody as shown in FIG. 15.

<3-2-1> Preparation of CD66c Mutant Recombinant DNA

CD66c mutant recombinant DNA was prepared using restriction enzyme BamHI existing in the epitope region of 8F5 antibody with pSec-Tag-CD66cfull-hFc recombinant DNA. Specifically, whole base sequence of the above CD66c antigen represented by SEQ ID No: 8 and hFc-conjugated gene were inserted to pSec-Tag, and this was ligated using restriction enzyme BamHI existing in the epitope region of 8F5 antibody to obtain CD66c mutant recombinant DNA.

More specifically, CD66c mutant (BI/BHI) that does not include epitope for 8F5 antibody was ligated with BamHI, and the above 252 bp between 535 and 787 bp of CD66c gene of SEQ ID No: 8 was removed and the rest of the fragment was connected again for the preparation. The sequence of CD66c mutant (BI/BHI) as prepared above is represented as SEQ ID No: 9.

Meanwhile, CD66c mutant (HPK/HdIII/PstI/klenow) which includes epitope of 8F5 antibody, but lacks parts of N domain and A domain in the N-terminus was prepared by ligation with Hind III and PstI, by removing 479 bp fragment from the N-terminus, by treating the rest of the gene fragment with Klenow to fill-in the sticky end for the HindIII and PstI to connect the blunt ends with each other. The sequence of CD66c mutant (HPK/HdIII/PstI/klenow) prepared as above is represented by SEQ ID No: 10.

<3-2-2> Expression of CD66c Mutant Recombinant DNA

The pSec-Tag vector inserted with the above CD66cfull-hFc, CD66c mutant (BI/BHI)-hFc, CD66c mutant (HPK/HdIII/PstI/klenow)-hFc was inserted into CHO-K1 cells using Effectene (Qiagen) for transformation.

More specifically, each of the above genes and Effectene complex were plated overnight, and sprayed with CHO cells with new media and cultivated for 48 hours. Two days after the above transfection, supernatant was obtained to confirm the expression by using sandwich ELISA for the detection of human Fc (hFc) (data not shown).

<3-2-3> Epitope Verification of the Monoclonal Antibody of the Present Invention In order to verify epitope of CD66c for monoclonal antibody of the present invention, conventional anti-CD66c antibodies, 9A6 (Santa cruz) and AP11 (DiNonA), were added in each well at 100 ng and reacted for 1 hour at 37° C. to coat as a capture antibody, and blocked by adding 200 μl of 1× blocking solution (sigma) and reacted for 1 hour at 37° C. After adding 100 μl/well of supernatants of CD66c full-hFc, CD66c mutant(BI BHI)-hFc and CD66c mutant (HPK/HdIII/PstI/klenow)-hFc prepared in the above Example 3-2-2 in the above prepared plate and reacting for 1 hour at 37° C., unconjugated antibody was removed by washing with PBS. In this, diluted anti-human Ig-HRP (Jackson) was added and reacted for 1 hour, wells were washed with PBS. TMB solution was added at 50 μl/well and reacted for 10 min, and the reaction was terminated by adding 50 μl of sulfuric acid to measure absorbance at 450 nm. To confirm the existence of CD66c mutant-hFc protein in the above supernatant, anti-human Ig antibody was used as a control group in Capture & Detect Sandwich ELISA. The results of the above experiment are shown in Table 5 and FIG. 16.

TABLE 5

| | | Capture antibody | | | |
| --- | --- | --- | --- | --- | --- |
| | | 8F5 | 9A6 | AP11 | a-huIg |
| media supernatant | CD66c full-hFc | 2.873 | 2.838 | 2.913 | 3.123 |
| | CD66c mutant (HPK/HdIII/PstI/klenow)-hFc | 2.804 | 0.049 | 0.097 | 3.113 |
| | CD66c mutant(BI/BHI)-hFc | 0.019 | 1.924 | 2.662 | 3.149 |
| | negative | 0.017 | 0.027 | 0.247 | 3.161 |

Figure 16:
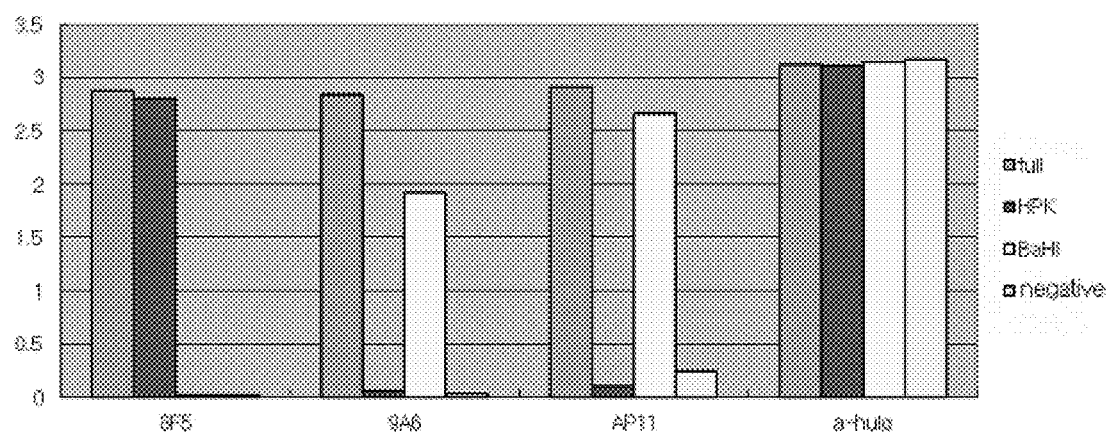
FIG. 16 is a result of verifying the epitope of the monoclonal antibody of the present invention.

As shown in the above Table 5 and FIG. 16, 8F5 antibody of the present invention has an activity to bind to CD66c full-hFc or CD66c mutant(HPK/HdIII/PstI/klenow)-hFc that contains the epitope verified in the above Example 3-1, but binds hardly with CD66c mutant(BI/BHI)-hFc without the above epitope. 9A6 and AP11, conventional CD66c antibodies, however, bonds mainly to CD66c mutant (BI/BHI)-hFc without the above epitope. Therefore, 8F5 antibody of the present invention is represented by a different epitope, amino acid sequence of SEQ ID No: 7, form the conventional 9A6 or AP11 antibody.

The above experimental result agrees accurately with epitope region of 8F5 antibody identified by MALDI-TOF as shown in FIG. 17.

EXAMPLE 4

Detection of Lung Adenocarcinoma Using Monoclonal Antibody of the Present Invention CD66c antigen was detected by using the monoclonal antibody of the present invention by immunoassay.

Specifically, AP11, a conventional antibody of CD66c was added at 100 ng/well and reacted for 1 hour at 37° C. to coat as capture antibody, and blocked by reacting with 200 μl/well of 1× blocking solution (sigma) for 1 hour at 37° C. In this prepared plate, 100 μg each of lysates of A549, an lung adenocarcinoma cell line, H417, a leukemia cell line, KatoIII (ATCC HB-103), a stomach cancer cell line, and K562 (ATCC CCL-243), a leukemia cell line were added and reacted for 1 hour at 37° C., and unconjugated antibody was removed by washing with PBS. In this, antibody prepared by conjugation of 8F5 antibody and HRP was added and reacted for 1 h. The plate was washed with PBS, reacted for 10 min after adding 50 μl/well of TMB solution and the reaction was terminated by adding 50 μl/well of sulfuric acid to read the value at 450 nm. The value (detection Ag) was determined quantitatively by using CD66c full-hFc as a standard, and the result is shown in FIG. 18.

Figure 18:
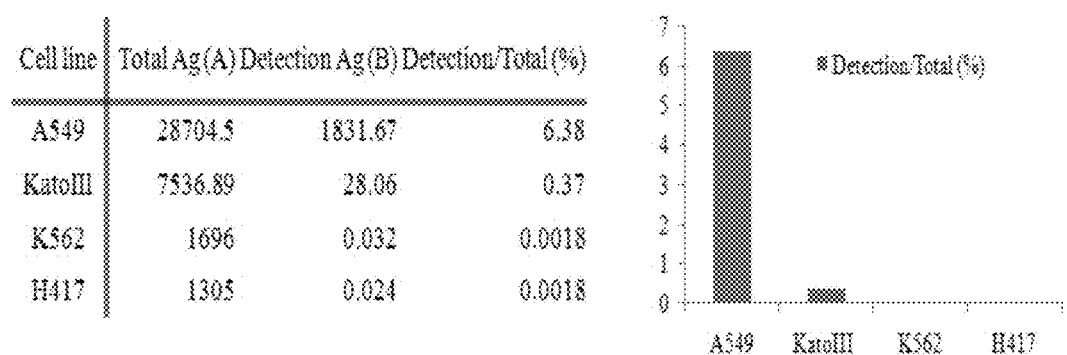
FIG. 18 is a result of detecting lung adenocarcinoma including CD66c antigen by using the monoclonal antibody of the present invention.

As shown in FIG. 18, lung adenocarcinoma can be detected efficiently by using 8F5 antibody of the present invention, and therefore it can be concluded that 8F5 antibody of the present invention is an effective lung adenocarcinoma specific biomarker.

EXAMPLE 5

CEACAM6 in A549 Correlated with Aggressiveness and Anoikis Resistance

Figure 19:
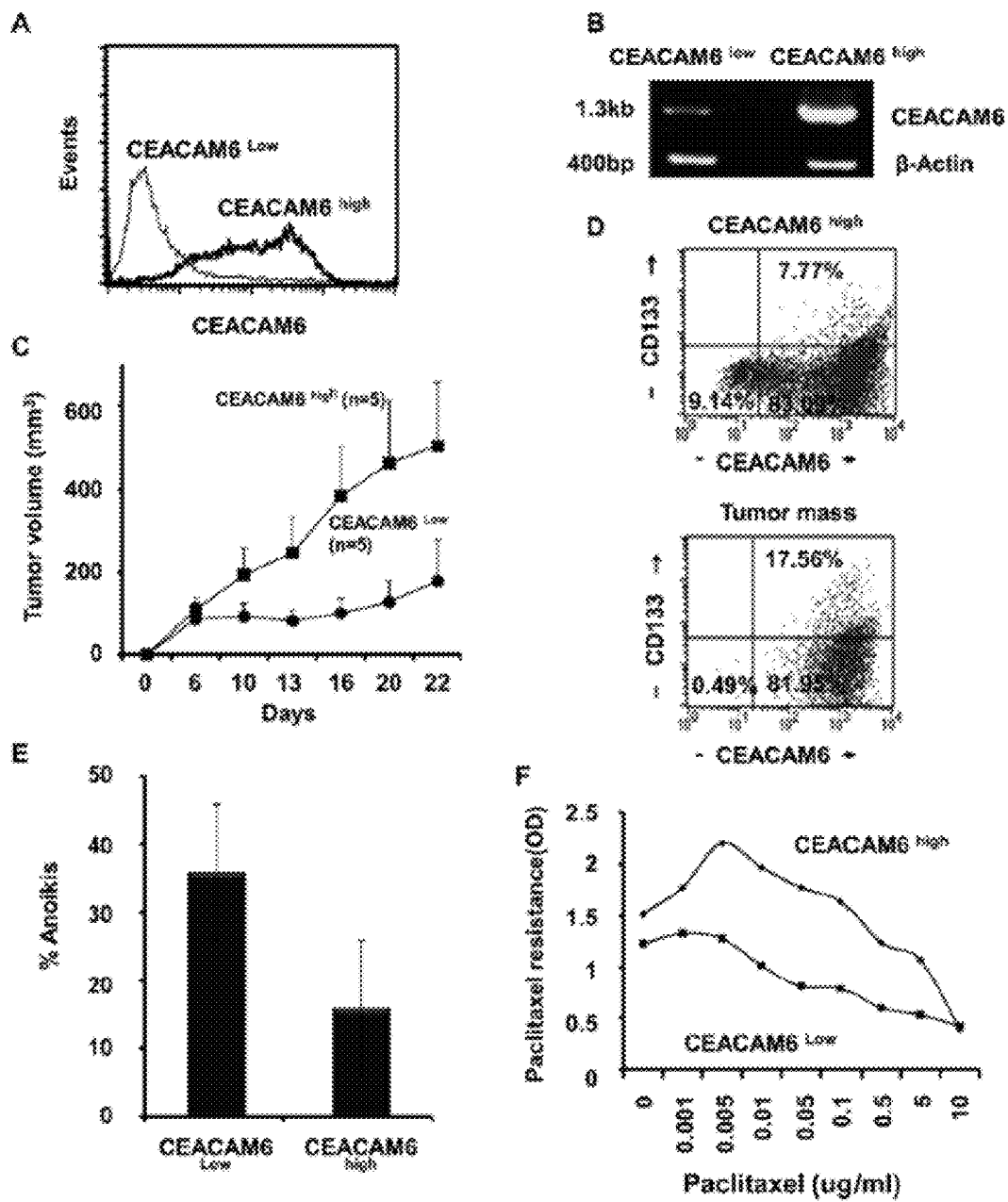
FIG. 19 illustrates the role of CD66c for tumorigenesis and chemosensitivity in lung adenocarcinoma according to Example 5.

We established CEACAM6 high and low A549 cell lines by repeated limiting dilution technique to investigate the role of CEACAM6 molecule on tumorigenesis in lung adenocarcinoma (FIG. 19A). The extent of CEACAM6 expression in the two cell lines established was further confirmed at both protein and RNA level (FIGS. 19A and 19B). CEACAM6 high A549 cells or CEACAM6 low A549 cells ($1\times10^7$ cells) were subcutaneously injected to nude mouse to compare the rate of tumor growth between the cells. As expected, CEACAM6 high A549 cell injected mice showed faster and larger tumor growth compared to mice injected with CEACAM6 low A549 cells (FIG. 19C). Next, we compared CEACAM6/CD133 double positive fractions before and after tumor formation using CEACAM6 high A549 cells to investigate the presence of CEACAM6 positive lung adenocarcinoma stem cells. The result revealed that proportion of CEACAM6/CD133 double positive stem cells were relatively increased after forming tumor mass (7.7% to 17.56%) (FIG. 19D). In addition, CEACAM6 high A549 cells demonstrate higher anoikis resistance and chemoresistance compared to CEACAM6 low A549 cells (FIG. 19E, F).

EXAMPLE 6

Anticancer Activity of Monoclonal Antibody of the Present Invention

<6-1> Anticancer Activity of Monoclonal Antibody of the Present Invention

Six-week old (18 g) male Nude-mouse (Central Lab. Animal Inc., Korea) was used for the experiment. A549, a lung adenocarcinoma cell line was suspended by using 1× trypsin-EDTA (GIBCO) and washed twice with Hanks balanced salt solution (HBSS) to inject $1\times10^7$ cell per mouse at the backside of the front leg at a volume of 100 µl to obtain inoculated mice. Before metastasis occurs, fast-growing tumor specimens with sufficient blood supply were obtained. The location of tumor was identified by touch on the skin, and the growth was observed at least twice a week, and the mice with 100 mm$^3$ of tumor mass in volume were used for the experiment.

To acquire high level of statistical significance, mice with higher than 100 mm$^3$ of tumor mass in volume were selected, and 10 mice were assigned per group. Monoclonal antibody of the present invention was diluted by 1×PBS and injected at a dose of 100 µg/100 µl, and administered for total 7 times at injection interval of 0, 3, 7, 14, 21, 28 and 35 days.

Figure 20A:
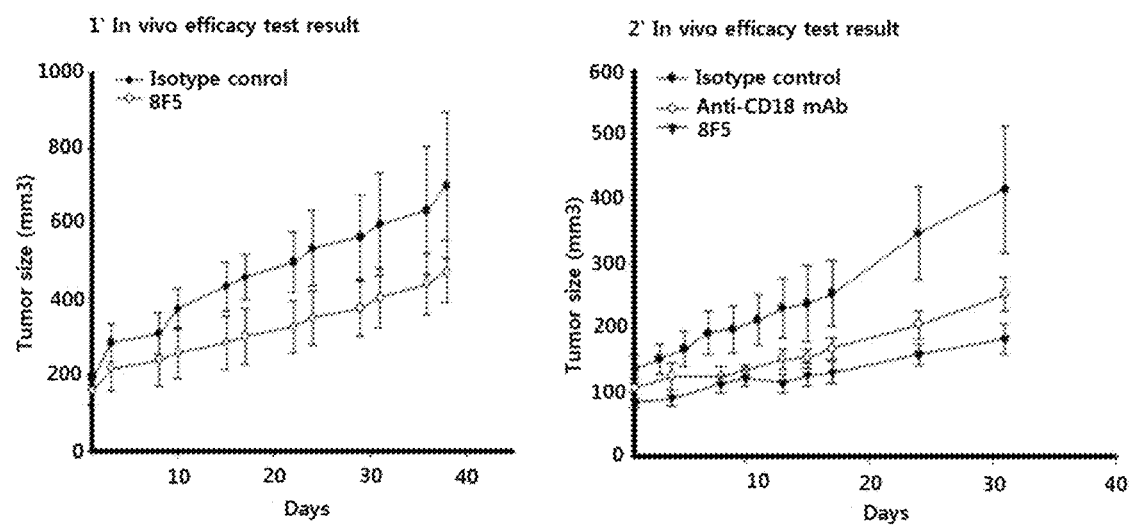
FIGS. 20a and 20b are a result of anticancer activity of the monoclonal antibody of the present invention.
Figure 20B:
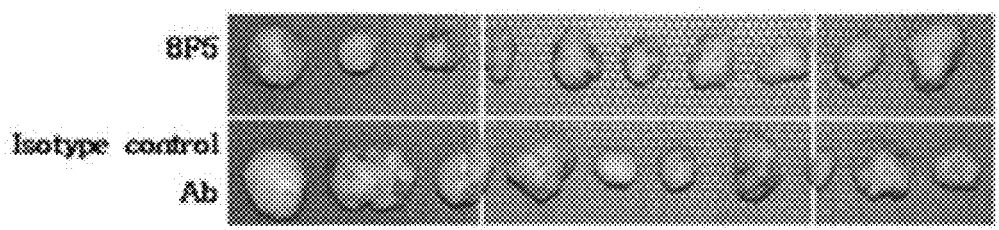

Volume of the tumor was estimated by measuring long and short axes with calipers twice a week starting at the administration day of the monoclonal antibody of the present invention for 4~5 weeks to verify the effect of the samples, and the result is shown in FIGS. 20a and 20b.

As shown in FIGS. 20a and 20b, 8F5 antibody of the present invention is an antibody that does not have antigen expressed in A549 cells, and has more than 30% higher anticancer effect than isotype control antibody (DiNonA) which has same isotype with 8F5.

<6-2> Anti-CEACAM6 Treatment Enhances Paclitaxel Chemo-Sensitivity In Vitro

Next, we examined if 8F5 mAb shows synergistic effect when treated in combination with several chemical drugs against lung adenocarcinoma. Amongst tested, 8F5 demonstrated most synergistic effect with paclitaxel, whereas only a weak or no synergy was observed with other chemicals. To investigate this synergistic effect further, CEACAM6 high A549 cells cultured in RPMI were treated with either increasing amounts of 8F5 with fixed concentration of Paclitaxel (FIG. 21G), or fixed amount of 8F5 with increasing concentration of Paclitaxel (FIG. 21H). As expected, 8F5 mAb treatment increased paclitaxel chemosensitivity at a dose dependent manner.

Figure 22A:
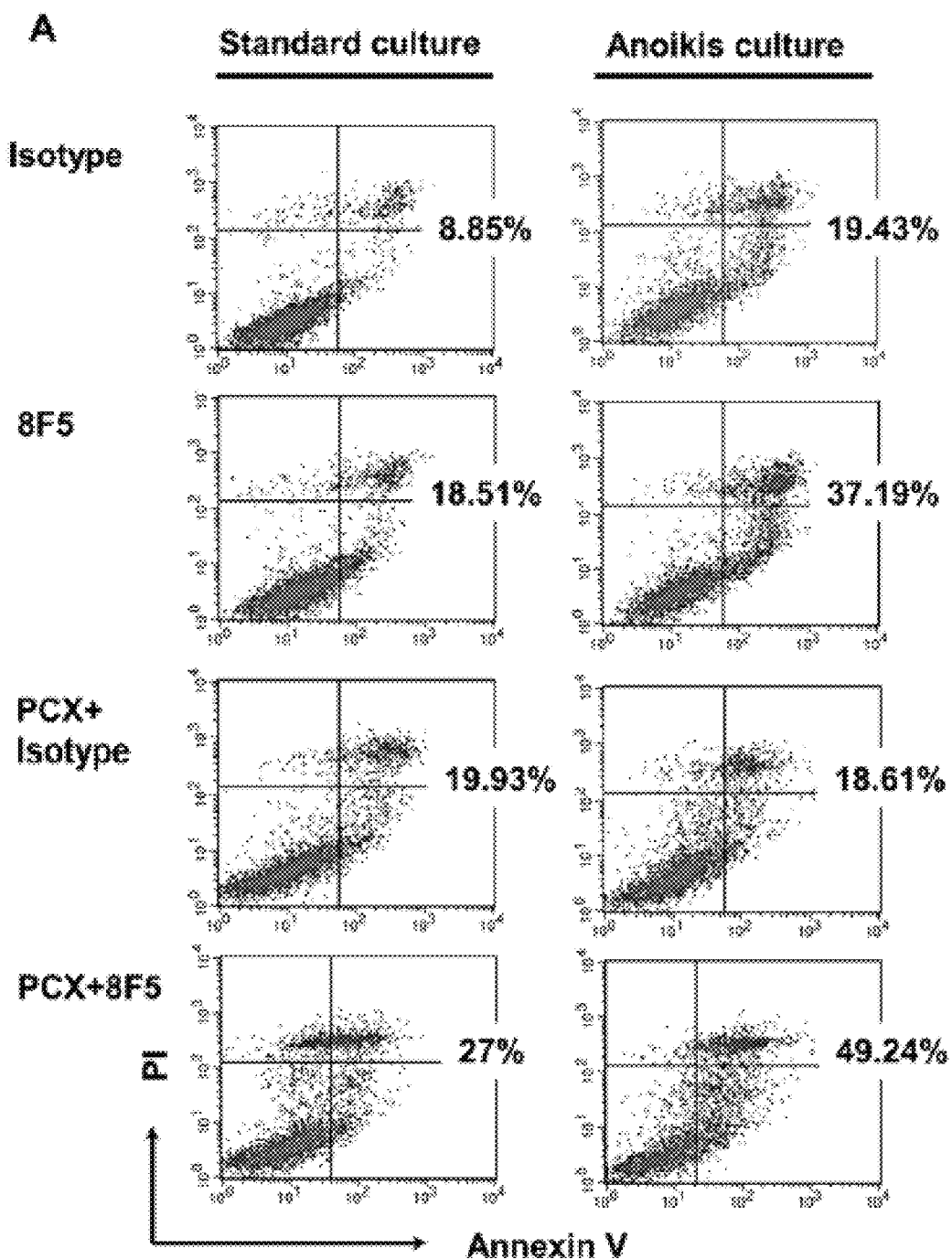
FIGS. 22a and 22b illustrate the apoptosis effect of the cells under the standard culture or anoikis culture conditions according to Example 6, in order to test the function of anti-CD66c monoclonal antibody in anoikis sensitivity.
Figure 22B:
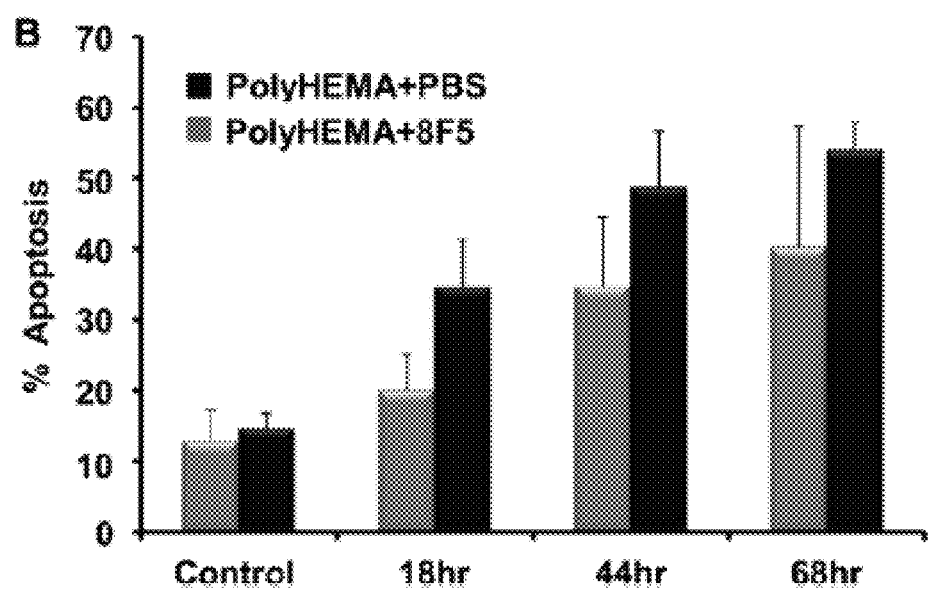

<6-3> Anti-CEACAM6 mAb Reversed Anoikis Resistance Via Down Regulation of CEACAM6 Expression To investigate the role of anti-CEACAM mAb treatment in anoikis sensitivity, we measured apoptosis in cells subjected to both standard and anoikis conditions (FIGS. 22a and 22b). Binding of anti-CEACAM6 mAb has increased anoikis population from 19.43% to 37.19%. Moreover, combination of mAb with Paclitaxel has shown a significant increase of anoikis from 18.61% to 49.24% (FIG. 22a). When cells were treated with either isotype mAb or isotype mAb with Paclitaxel, cells demonstrated 19.43% and 18.61% anoikis, respectively. Cells exhibited increasing anoikis activity in time dependent manner (FIG. 22b).

Figure 23A:
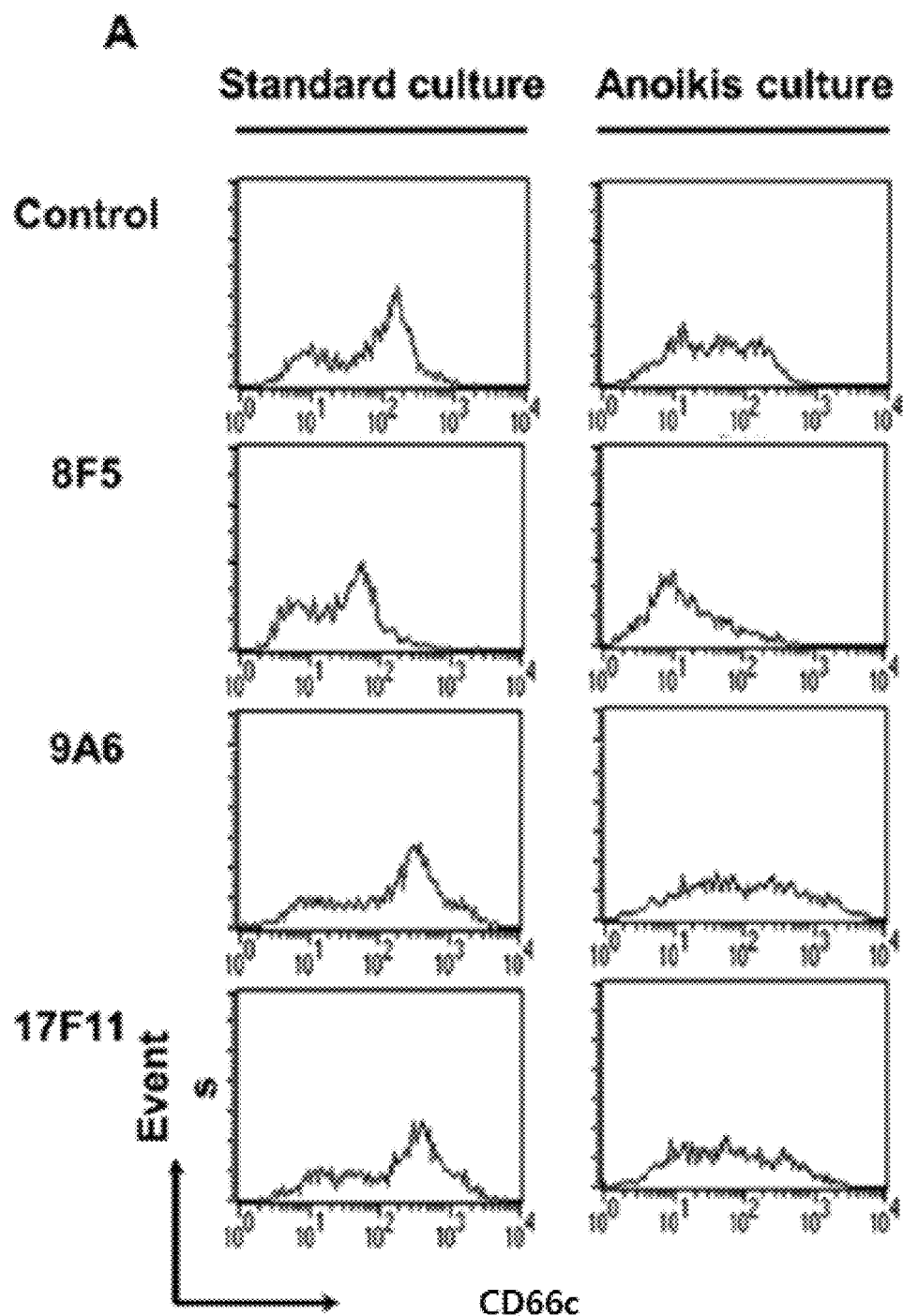
FIGS. 23a and 23b illustrate the expression level of CD66c protein by using flow cytometer to investigate whether the anti-CD66c antibody influences the activity of CD66c protein by binding to the CD66c and regulating its expression level in a cell, according to Example 6.
Figure 23B:
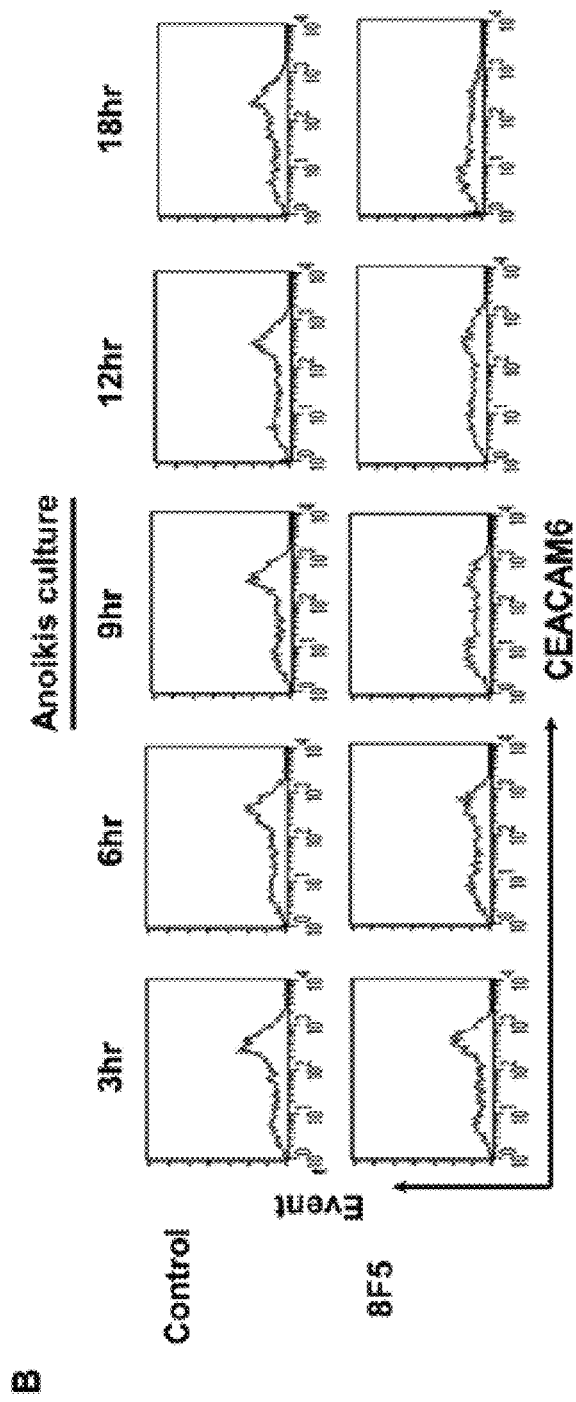

To investigate whether binding of mAb exerts its activity via modulating cellular expression level of CEACAM6, we measured its expression by flow cytometry. To our surprise, the binding of 8F5 caused a significant decrease in CEACAM6 expression, whereas anti-CEACAM6 mAbs specific to N domain (9A6 and 17F11) did not (FIGS. 23a and 23b).

Anoikis was induced by polyHEMA (Sigma, St Louis, Mich., USA) culture. A solution of 120 mg/ml polyHEMA in 100% ethanol was prepared and diluted 1:10 in 95% ethanol; 0.95 µl/mm$^2$ of this solution was pipetted into 6 and 12 wells and left to dry for 48 h at room temperature. Prior to use, wells were washed twice with PBS and once with RPMI. Cells at 2~5×10$^5$ cells/1 ml RPMI (10% FBS) per well density were added with 8F5 mAb, goat-anti-mouse IgG (10 µg/ml), and paclitaxel (0.5 µg/ml) and incubated in polyHEMA-coated wells for various length of times in a humidified incubator (37° C., 5% CO$_2$). Following induction of anoikis, cells were washed, resuspended in 0.5 ml of PBS, and added with 5 µl annexin V and 10 µl propidium iodide (BD, Annexin V-FITC Apoptosis Detection Kit, USA). Cells were incubated for 15 min in dark, followed by analysis using flow cytometry (FACS Calibur, Becton Dickinson). CEACAM6 high A549 cells were pre-incubated at 37° C. for 1 hour with 100 µM of caspase 3, 8, 9, or 10 inhibitor (R&D, USA) in polyHEMA coated plate, followed by addition of 8F5 mAb and IgG (10 µg/ml) and incubation for 18 h at 37° C. Following induction of anoikis, cells were washed, resuspended in 0.5 ml of PBS, and added with 5 µl annexin V and 10 µl propidium iodide. Cells were incubated for 15 min in dark, followed by analysis using flow cytometry.

Determining cancer stem cell population is performed by flow cytometer. Tumor bearing mice were sacrificed and the tumor dissected. Freshly collected tumor mass was maintained in RPMI (10% FBS) at 4° C. until processed. Single cells were isolated by rinsing and chopping the solid tumor mass. Cells in suspension were pelleted, resuspended using RPMI (10% FBS), and centrifuged at room temperature for 5 min at 1700 rpm. After 2 washes with RPMI (10% FBS), tumor cells were resuspended in 1×10⁶/100 μl PBS and added to normal mouse serum, followed by incubation for 10 min at 4° C. Anti-CEACAM6-FITC and anti-CD133-PE (BD Biosciences, USA) were added to the cells and incubated for 15 min at 4° C. After washing with PBS, cells were analyzed using flow cytometry (FACS Calibur, Becton Dickinson, USA).

<6-4> Binding of Anti-CEACAM6 mAb Decreased Akt Phosphorylation and Induced Apoptosis Via Caspase Activation To evaluate if 8F5 mAb binding induces direct modulation of signaling pathway in A549 cells, we examined the Akt phosphorylation status. In cell treated with 8F5 mAb alone, and 8F5 co-treated with Paclitaxel, we observed a marked decrease in Akt phosphorylation (FIG. 24C).

Figure 24:
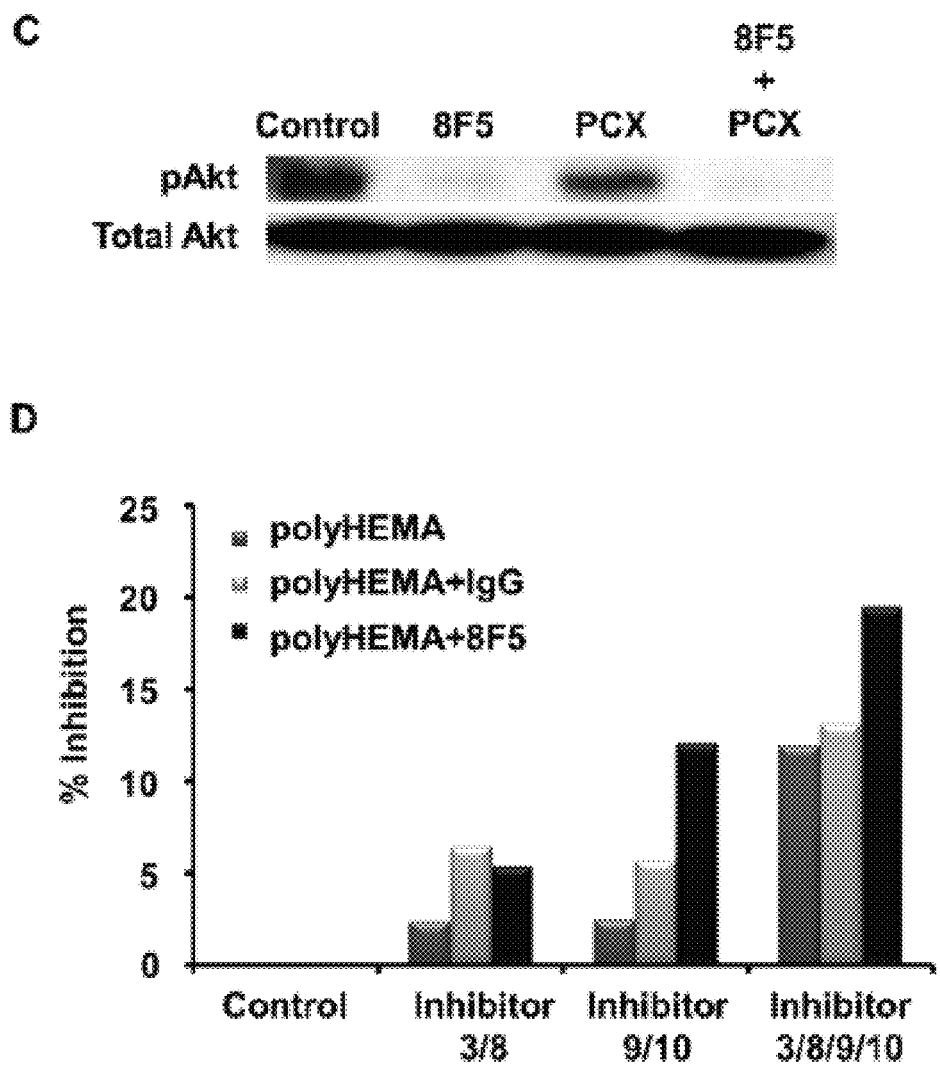
FIG. 24 illustrates the phosphorylation state of Akt protein to investigate whether the binding of 8F5 monoclonal antibody directly regulates the signaling pathway in A549 cells, according to Example 6.

To examine whether enhancement of anoikis by 8F5 mAb is associated with caspase activity, we treated A549 cells with inhibitors of caspases 3/8, 9/10, or 3, 8, 9, and 10 in the presence or absence of 8F5 (FIG. 24D). Result showed that 8F5 induced enhancement of anoikis via caspase 9 and 10 dependent pathway.

Figure 25A:
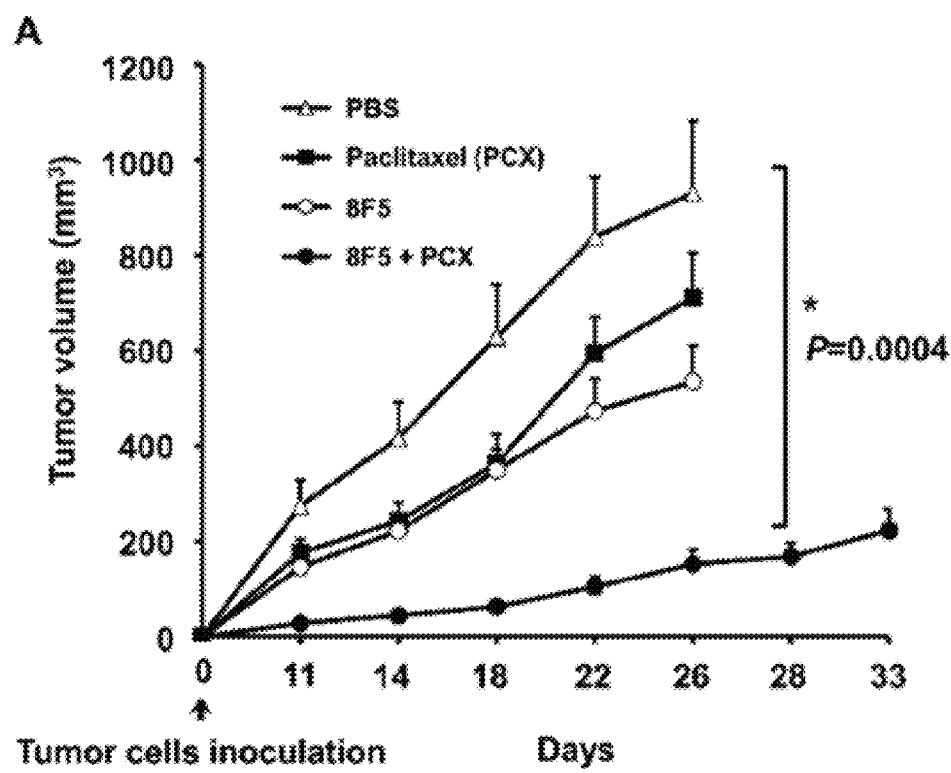

<6-5> Anti-Tumor Effect Exhibited by Combined Treatment of Anti-CEACAM6 mAb and Paclitaxel in A549 Xenograft Model We next evaluated the antitumor effect of anti-CEACAM6 mAb with paclitaxel by studying tumor growth using A549 xenotransplanted mice. When mAb was added in the beginning of tumor cell inoculation in absence or presence of paclitaxel, a significant inhibition in tumor growth was noted (FIG. 25A, C). In particular, the combined injection of 8F5 mAb with paclitaxel showed a significant tumor growth inhibition of 80% (p<0.0004), whereas 8F5 mAb alone demonstrated 40% tumor growth inhibition compared to PBS control (FIG. 25a). When the treatment was administered after tumor mass has reached 200 mm3, this effect was less pronounced, with combined treatment of 8F5 mAb and paclitaxel showed 50% tumor growth inhibition compared to PBS control (FIG. 25b).

What is claimed is:

1. A method of treating a lung cancer, comprising administering an anti-CD66c (Cluster of Differentiation 66c) antibody being specific to a lung adenocarcinoma or an antigen-binding fragment thereof, and a chemotherapeutic agent as effective agent, to a subject in need, wherein the anti-CD66c antibody is an antibody produced by hybridoma cell deposited as an accession number of KCLRF-BP-00230, and wherein the chemotherapeutic agent is paclitaxel.

2. The method of claim 1, wherein the antigen-binding fragment is Fab, Fab', F(ab')2, scFv, (scFv)2, scFvFc or dsFv.

3. The method of claim 1, wherein the lung cancer is lung adenocarcinoma, Squamous cell carcinoma of lung, epithelial lung cancer, small cell lung cancer or non-small cell lung cancer.

4. The method of claim 1, wherein the anti-CD66c antibody and the chemotherapeutic agent are administered in a mixed formulation, or administered simultaneously or sequentially in single formulation.

5. The method of claim 1, wherein the anti-CD66c antibody is formulated for oral administration and the chemotherapeutic agent is formulated for parenteral administration.

6. The method of claim 1, wherein the anti-CD66c antibody is formulated for injectable administration.

* * * * *